United States Patent
Gangadharmath et al.

(10) Patent No.: US 10,639,608 B2
(45) Date of Patent: May 5, 2020

(54) SYSTEM, DEVICE AND METHOD FOR PREPARING TRACERS AND TRANSFERRING MATERIALS DURING RADIOSYNTHESIS

(75) Inventors: Umesh B. Gangadharmath, Los Angeles, CA (US); Joseph C. Walsh, Pacific Palisades, CA (US); Hartmuth C. Kolb, Playa Del Rey, CA (US); Ricardo Rodriguez, Hacienda Heights, CA (US); Arkadij M. Elizarov, Woodland Hills, CA (US); Carroll Edward Ball, Mission Viejo, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1119 days.

(21) Appl. No.: 13/445,147

(22) Filed: Apr. 12, 2012

(65) Prior Publication Data

US 2012/0283490 A1    Nov. 8, 2012

Related U.S. Application Data

(63) Continuation-in-part of application No. PCT/US2011/031681, filed on Apr. 8, 2011.
(Continued)

(51) Int. Cl.
*B01J 19/00* (2006.01)
*C07B 59/00* (2006.01)
(Continued)

(52) U.S. Cl.
CPC ......... *B01J 19/004* (2013.01); *A61K 51/0455* (2013.01); *A61K 51/08* (2013.01);
(Continued)

(58) Field of Classification Search
CPC ........ B01J 19/08; B01J 19/081; B01J 19/004; G01N 35/1009; G01N 35/1011
(Continued)

(56) References Cited

U.S. PATENT DOCUMENTS 5,380,486 A * 1/1995 Anami ............... G01N 35/1079
                                                                422/513
6,172,207 B1 * 1/2001 Damhaut et al. ............ 536/18.4
(Continued)

FOREIGN PATENT DOCUMENTS

WO    2008101305    8/2008
WO    2009003251    1/2009
(Continued)

OTHER PUBLICATIONS

Joël Aerts et al., "Fast production of highly concentrated reactive [18F] fluoride for aliphatic and aromatic nucleophilic radiolabeling", Tetrahedron Letters, vol. 51, pp. 64-66 (2009).
(Continued)

*Primary Examiner* — Jill A Warden
*Assistant Examiner* — Dwayne K Handy

(57) ABSTRACT

A system, apparatus, and method for transferring chemical solutions and synthesizing a tracer. For transferring chemical solutions, the system comprises a primary container; a secondary container; a first line in communication with the primary container and the secondary container. The first line facilitates the flow of gas and/or liquid between the primary container and the secondary container. A valve located upstream of the secondary container and downstream of the primary container regulates flow within the first line; a second line in communication with the secondary container. For synthesizing a tracer, the system includes a source of a solution having a radionuclide. A first container has a tracer precursor and is in communication with the source of solution.

14 Claims, 8 Drawing Sheets

Related U.S. Application Data

(60) Provisional application No. 61/497,190, filed on Jun. 15, 2011, provisional application No. 61/474,804, filed on Apr. 13, 2011, provisional application No. 61/322,074, filed on Apr. 8, 2010.

(51) Int. Cl.
*B01J 4/00* (2006.01)
*A61K 51/08* (2006.01)
*A61K 51/04* (2006.01)

(52) U.S. Cl.
CPC ............ *A61K 51/082* (2013.01); *B01J 4/008* (2013.01); *C07B 59/00* (2013.01); *Y10T 137/86035* (2015.04)

(58) Field of Classification Search
USPC ................. 422/71, 509, 527, 129, 130, 159; 424/1.11, 9.3
See application file for complete search history.

(56) References Cited

U.S. PATENT DOCUMENTS

| | | | |
|---|---|---|---|
| 7,022,872 | B2 | 4/2006 | Walsh et al. |
| 7,160,637 | B2 | 1/2007 | Chiao et al. |
| 7,419,653 | B2 | 9/2008 | Walsh et al. |
| 7,666,392 | B2 | 2/2010 | Kolb et al. |
| 7,807,394 | B2 | 10/2010 | Kolb et al. |
| 7,829,063 | B2 | 11/2010 | Kolb et al. |
| 7,928,210 | B2 | 4/2011 | Kolb et al. |
| 2004/0022696 | A1* | 2/2004 | Zigler et al. .................. 422/159 |
| 2004/0236085 | A1 | 11/2004 | Luthra et al. |
| 2006/0245980 | A1* | 11/2006 | Kiselev ...................... A61J 3/00 422/130 |
| 2008/0170993 | A1 | 7/2008 | Srinivasan et al. |
| 2009/0036668 | A1 | 2/2009 | Elizarov et al. |
| 2010/0074843 | A1 | 3/2010 | Kolb et al. |
| 2010/0239496 | A1 | 9/2010 | Gangadharmath et al. |
| 2011/0008215 | A1 | 1/2011 | Elizarov et al. |
| 2011/0150714 | A1 | 6/2011 | Elizarov et al. |
| 2011/0182812 | A1 | 7/2011 | Szardenings et al. |
| 2013/0144051 | A1* | 6/2013 | Mueller ................. B01J 19/004 536/122 |

FOREIGN PATENT DOCUMENTS

| | | |
|---|---|---|
| WO | 2009059977 | 5/2009 |
| WO | 2011119565 | 9/2011 |
| WO | 2011127345 | 10/2011 |

OTHER PUBLICATIONS

Hyung Woo Kim et al., "Rapid synthesis of [18F]FDG without an evaporation step using an ionic liquid", Applied Radiation and Isotopes, vol. 61, pp. 1241-1246 (2004).

Dong Wook Kim et al., "A New Class of SN2 Reactions Catalyzed by Protic Solvents: Facile Fluorination for Isotopic Labeling of Diagnostic Molecules", J. Am. Chem. Soc., vol. 128, No. 50, pp. 16394-16397 (Nov. 23, 2006).

Haubner et al., "[18F]Galacto-RGD: Synthesis, Radiolabeling, Metabolic Stability, and Radiation Dose", Bioconjugate Chem. 2004, 15, 61-69.

Lemaire, et al., "Fast Production of Highly Reactive No-Carrier-Added [18F] Fluoride for the Labeling of Radiopharmaceuticals", In Angewandte Chemie (International Ed. in English) vol. 49, No. 18, Mar. 25, 2010, pp. 3161-3164.

Cogneau, et al., "Production of a High Purity <18>F Radioactive Beam", In Nuclear Instruments and Methods in Physics Research, Section A—Accelerators, Spectrometers, Detectors and Associated Equipment. vol. 420, No. 3, Jan. 11, 1999, pp. 489-493.

S. John Gatley., "Rapid Production and Trapping of [<18>F]Fluorotrimethylsilane, and Its Use in Nucleophilic Fluorine-18 Labeling Without an Aqueous Evaporation Step", In Applied Radiation and Isotopes, International Journal of Radiation Applications and Instrumentation, Part A, vol. 40, No. 6, Jan. 1, 1989, pp. 541-544.

Liu Y, et al., "Optimization of automated radiosynthesis of [<18>F]AV-45: a new PET imaging agent for Alzheimer's disease", Nuclear Medicine and Biology, Elsevier, NY, US, vol. 37, No. 8, Nov. 1, 2010, pp. 917-925.

Oh S.J., et al., "Fully automated synthesis system of 3'-deoxy-3'-[<18>F] fluorothymidine", Nuclear Medicine and Biology, Elsevier, NY, US, vol. 31, No. 6, Aug. 1, 2004, pp. 803-809.

Search report of European Patent Application No. 14 17 4712 dated Oct. 17, 2014.

\* cited by examiner

SCHEMATIC OF THE PNEUMATIC DEVICE USED FOR PREPARING T807

SYSTEM, DEVICE AND METHOD FOR PREPARING TRACERS AND TRANSFERRING MATERIALS DURING RADIOSYNTHESIS

RELATED APPLICATIONS

This application is a continuation-in-part of PCT/US2011/31681, "Synthesis of $^{18}$F-Labeled Tracers in Hydrous Organic Solvents," which claims priority to U.S. Ser. No. 61/322,074. These applications are incorporated by reference in their entirety. The present application also claims priority to Provisional Application No. 61/474,804, filed on Apr. 13, 2011 and Provisional Application No. 61/497,190, filed on Jun. 15, 2011, the entirety all of which are incorporated herein by reference.

FIELD OF THE INVENTION

The present disclosure relates to diagnostic imaging, in particular Positron Emission Tomography (PET) or Single-Photon Emission Computed Tomography (SPECT). More specifically, it relates to a system, apparatus and method for transferring chemical solutions and synthesizing radiopharmaceuticals. More specifically, the present disclosure relates to apparatuses for synthesizing of probes for imaging such as by Positron Emission Tomography (PET) or Single-Photon Emission Computed Tomography (SPECT). More specifically, the present disclosure is directed to a simplified apparatus for synthesizing probes, such as $^{18}$F-labeled probes. The apparatus may be used to make radiolabeled tracers using the method described in PCT/US11/31681, the entirety of which is incorporated herein by reference, or other methods.

BACKGROUND

The use of positron-labeled tracers for the diagnosis, staging and monitoring of various diseases using, for example, Positron Emission Tomography (PET) has grown in use over the past 20 years. Examples of some widely used, clinically approved imaging agents include [F-18]FDG, [F-18]NaF and [F-18]Fluoro-DOPA. Several other tracers, while not clinically approved, are being used for investigational purposes. Examples of these tracers include [F-18]FLT and [F-18]AV-45.

Typically, the radiosynthesis of positron-radiotracers are performed remotely behind lead-shielded containers using automated, semi-automated or manual synthesis instrumentation. Large amounts of lead shielding are required to protect the operators from radiation emitted by the labeling isotopes. As a consequence, all of the hardware, reagents and plumbing must be prepared and readied prior to the introduction of radioactivity into the synthesis platform. Unprotected interventions by the operator into areas containing large amounts of radioactivity for the purposes of making hardware adjustments, addition of reagents or facilitating the transfer of materials are heavily discouraged.

For routine syntheses, the need for operator intervention is minimized because the chemistry is well supported by the instrumentation's hardware. For example, the synthesis of well-established radiotracers follows a well-defined protocol of isotope activation (eg. preparing anhydrous [F-18]fluoride), labeling, deprotection (if required), purification and formulation for injection. Such well known protocols are used for making several common tracers known in the art such as [F-18]FDG, [F-18]FLT, [F-18]FHBG and [F-18]MISO.

In general, a drawback of the synthesis of these radiolabeled molecules is undoubtedly time consuming, labor intensive and randomly unreliable. In addition, highly complex and expensive instrumentation is required for successful production of these tracers. In an effort to minimize production and cost issues, radiochemists have attempted to reduce the labeling procedures to their simplest, quickest and most reliable protocols on mechanically simple platforms. Despite these process improvements, radiolabeling protocols still contain inherent inefficiencies that would benefit from further chemistry, process and hardware improvements.

Currently available platforms designed to produce radiolabeled compounds are typically complex and inefficient, which are not suitable to fit for newly developed processes. For example, PCT/US11/31681 describes a procedure where a solvent with a predetermined amount of water in at least one organic solvent is used to a) elute the $^{18}$F-fluoride from an anion exchange cartridge and h) perform the $^{18}$F-labeling, without drying the $^{18}$F-fluoride, in the presence of at least one labeling reagent and at least one phase transfer catalyst. In other methods, the $^{18}$F-fluoride solution may be dried. The incorporation of hydrous labeling protocols, such as that described in PCT/US11/31681, is not easily transferable to existing synthesis platforms for the reason that these platforms were not designed for such protocols. For example, for anhydrous protocols, existing apparatuses comprise many unnecessary components. Fluid paths and valves are superfluous and provide little or no benefit in supporting the chemistry.

Conventional platforms for making FDG have several features in common as their processes follow well-established protocols. To begin with, anion exchange cartridges sequester [F-18]fluoride ion from [O-18]water. The trapped [F-18]fluoride ion is then released from the anion exchange cartridge into a reaction vessel. A typical anion exchange cartridge may include a Quaternary Methylammonium Anion exchange cartridge (QMA). The vessel is then heated under a stream of an inert gas such as nitrogen to remove the excess moisture. Once the moisture is sufficiently removed, then a labeling precursor is added, typically as a solution in an organic solvent. The reaction mixture is then heated for a period of time to induce the nucleophilic addition of [F-18]fluoride onto the labeling precursor. After this labeling is finished, there is an optional series of post-labeling processing steps which may include a deprotection and or neutralization step. The contents of the reaction vessel are then transferred out for post-labeling purification. For simple purifications, a series of small cartridges are used to remove unwanted by-products, adjust pH and render the dose suitable for injection. For more complex purifications, typically reverse-phase High Performance Liquid Chromatography (HPLC) purification is performed with an optional reformulation of the isolated HPLC fraction to render the dose suitable for injection. There are variations between different types of synthesis platforms at each step of the production protocol. For instance, some platforms employ vacuum to assist in the evaporation of moisture during the [F-18]fluoride drying step, while other platforms simply use inert gas without the aid of negative pressure. However, methods and hardware employed for preparing this moisture-free [F-18]fluoride are not necessary.

The conventional means for $^{18}$-labeling involves the formation of "activated" or "naked" fluoride, i.e. fluoride that is sufficiently moisture-free and thus suitable for radiolabeling. It is widely known that the desolvation of fluoride increases its nucleophilic character. See V. M. Vlasov, "Fluoride ion as a nucleophile and a leaving group in aromatic nucleophilic substitution reactions", J. of Fluorine Chem., vol. 61, pp. 193-216 (1993). In these conventional labeling protocols, trace amounts of $^{18}$F-fluoride are sequestered onto an anion exchange column from several milliliters of $^{18}$O-water. Afterwards, the $^{18}$F-fluoride ion is eluted from the anion exchange column through the use of salts, such as $K_2CO_3$, dissolved in water. An additive/catalyst such as the potassium crown ether Kryptofix™ K222, which is dissolved in anhydrous acetonitrile, may be used in conjunction with aqueous $K_2CO_3$ to facilitate the elution of $^{18}$F-fluoride, or optionally added into the reaction vessel after the $K_2CO_3$-mediate elution.

After the elution step, there is an extensive drying protocol needed as reagents $K_2CO_3$ and Kryptofix™ K222 are in a highly hydrous solution of acetonitrile. This drying step generates an activated mixture of $K_2CO_3$, Kryptofix™ K222 and $^{18}$F-fluoride. The drying process begins by evaporating the azeotropic mixture at elevated temperatures, oftentimes at reduced pressures to aid in the evaporation of water from the reaction vessel. This initial drying can take up to 30 minutes to complete, depending on the efficiency of drying. After the first evaporation, it may be necessary to perform additional evaporations to effectively remove of enough water to render the $^{18}$F-fluoride sufficiently moisture-free for labeling.

There are several inherent problems with this approach to generating activate reagents for $^{18}$F-fluorination. First, the amount of residual water after the initial drying step may vary from run-to-run given mechanical differences in vacuum, gas flows, valve integrity and temperature control. Mechanical problem, either a single one or combination of a few, will negatively impact the efficiency of drying and hence, the labeling results. Since the amount of residual water could vary greatly from run to run, the radiolabeling results would then be inconsistent, making reliable production of radiotracers difficult. Also, given the time needed to successfully dry the fluoride, a good portion of the total synthesis time is dedicated to the drying step. Lastly, because of the concern of residual water in the reaction, there is a potential for operators to "overdry" the reaction mixture prior to fluorination. In this instance, drying the reagents for too long may be as equally hurtful as under-drying the reagents (under-drying being the failure to remove sufficient moisture from the reagents for $^{18}$F-fluorination). For example, Kryptofix™ K222 decomposition is directly related to drying times and temperatures: prolonged drying at high temperature compromises the integrity and functionality of Kryptofix™ K222. To address these issues, a method that minimizes the length of drying and can accurately control the amount of moisture from run to run would be a substantial improvement to current radiolabeling practices.

Alternate methods have been developed in an attempt to obviate the need for the drying step that either elute $^{18}$F-fluoride from anion exchange resins using additives in either anhydrous organic solvents (such as acetonitrile, see Joel Aerts et al., "Fast production of highly concentrated reactive [$^{18}$F] fluoride for aliphatic and aromatic nucleophilic radiolabeling", Tetrahedron Letters, vol. 51, pp. 64-66 (2009); International Patent Application Pub. No. WO 2009/003251) or by using ionic liquids in hydrous acetonitrile (Hyung Woo Kim et al., "Rapid synthesis of [$^{18}$F]FDG without an evaporation step using an ionic liquid", Applied Radiation and Isotopes, vol. 61, pp. 1241-1246 (2004)). For these types of elutions using compounds with unknown toxicities, one would want to assay for these additives in the final product prior to injection and imaging, which ultimately complicates the production workflow.

Efforts to increase the yield of the synthesis have also been reported. The use of hydroalcoholic (i.e. protic solvents) co-mixtures is reported to improve $^{18}$F-labeling yields over the standard single solvent IT-labeling conditions. Dong Wook Kim et al., "A New Class of $S_N2$ Reactions Catalyzed by Protic Solvents: Facile Fluorination for Isotopic Labeling of Diagnostic Molecules", J. Am. Chem. Soc., vol. 128, no. 50, pp. 16394-16397 (Nov. 23, 2006). While the increases in yields are believed to be a result of the unique interactions between the $^{18}$F-fluoride and possibly the leaving group on the precursor, it is not practical to use hydroalcoholic solvents, such as t-amyl alcohol, as they must be analyzed in the final product. Additionally, the low polarity of these bulky solvents can hinder the precursor's solubility which can be used for the labeling reaction, thus negatively impacting the radiolabeling yield.

In addition to the complicated activation of [F-18]fluoride, existing synthesis platforms often utilize expensive components that require constant cleaning from run-to-run. This process may consume additional reagents, time and lifespan of the individual components. Most systems require regular (e.g., quarterly) maintenance, which is costly and takes the machine out of operation for a period of time. Removal of this cleaning protocol has several distinct advantages.

Moreover, the field of PET chemistry is also always evolving with the development of new tracers. These tracers can possess more efficient imaging characteristics than previous agents or may target novel diseases or biochemistry not previously known or targeted. With the advent of new tracers, new chemistries often evolve without the hardware supporting the preparation of these new tracers. Therefore, it is common for developmental runs to be performed at low levels of radioactivity with several manual operations needed in order to find a suitable protocol for production.

Oftentimes, new chemistries are often utilized without the convenience and safety of dedicated hardware. As an example, the synthesis of galacto-RGD is shown in "[18F] Galacto-RGD: Synthesis, Radiolabeling, Metabolic Stability, and Radiation Dose", Haubner et al., Bioconjugate Chem. 2004, 15, 61-69. Estimates were not easily automated requiring many manual interventions. As a result, there is in an increased risk for radiation exposure to the operator during these intervening operations. As a second example of new chemistries not supported by current instrumentation, the increased use of click chemistry oftentimes occurs on synthesis platforms not fully equipped to support the necessary transfers of radioactivity, again increasing the risk of radiation exposure to the operator during the intervention steps.

Therefore, there is a need for systems that support new radiolabeling chemistries in a safe and efficient manner. There is also a need for a synthesis module that is inexpensive to manufacture, efficient, free of unnecessary components, reliably produces labeled tracers and has components that are easily disposable. For example, simpler and more efficient designs are desirable to support efficient and simple radiolabeling protocols such as those described in PCT/US11/31681

SUMMARY

An embodiment as set forth in the present disclosure is directed to a system for transferring chemical solution, the system comprising a primary container; a secondary container; a first line in communication with the primary container and the secondary container, the first line configured to facilitate the flow of gas and/or liquid between the primary container and the secondary container; a valve upstream of the secondary container and downstream of the primary container, the valve configured to regulate flow within the first line; a second line in communication with the secondary container; and a pressure source in communication with the primary container, the pressure source configured to drive gas and/or liquid to the secondary container via the first line; wherein the first line and the second line are configured to move within the secondary container.

Another embodiment as set forth in the present disclosure is directed to an apparatus for transferring chemical solution, the apparatus comprising: a container configured to contain chemical reagents, reaction intermediates and/or reaction products; a first line in communication with the container, the first line configured to deliver the chemical reagents, reaction intermediates and/or reaction products to the container; and a second line in communication with the container, wherein the first line and second line are configured to move toward and away from the bottom of the container.

Yet, another embodiment as set forth in the present disclosure is directed to a method of transferring chemical solution, the method comprising: providing a source of chemical reagents, reaction intermediates and/or products; providing a container; providing a pressure source configured to move chemical reagents, reaction intermediates and/or products into the container; providing a first line in communication with the source of chemical reagents, reaction intermediates and/or products and the container; providing a second line in communication with the container, wherein the first line and the second line are configured to move relative to the container, positioning the first line so that it interacts with chemical reagents, reaction intermediates and/or products when they are introduced into the container; positioning the second line so that with the second line is excluded from interacting with the chemical reagents, reaction intermediates and/or products when they are introduced into the container; transferring the chemical reagents, reaction intermediates and/or products to the container through the first line, via pressure from the pressure source, such that the first line is in contact with the chemical reagents, reaction intermediates and/or products and the second line is out of contact with the chemical reagents, reaction intermediates and/or products; moving the first line out of contact with the chemical reagents, reaction intermediates and/or products; and moving the second line in contact with the chemical reagents, reaction intermediates and/or products.

Yet, another embodiment as set forth in the present disclosure is directed a device that allows for the remote manipulation and materials transfer for the purposes of supporting a broader array of chemistries while reducing the chances of the operator being exposed to something harmful such as radiation. More specifically, this device controls the transfer of materials from a primary reaction pot, container or vial into a secondary vial or container. The types of materials that can be easily transferred include reagents, reaction mixtures, solvents and distillates. Because the unit is controlled remotely behind leaded shielding, the operator is protected from radioactive exposure.

In one embodiment, the device includes multiple movable arms connected to lines that may be independently moved, for example, lowered and/or raised. The lines are preferably situated in the secondary vial (marked as "a" and "b"). The device may have cooling and heating units in order to control the temperature within the secondary vial. The device may be optionally equipped with a stirrer (to agitate the contents of the secondary vial) and/or a radioactivity detector (to monitor the activity transferred into, and out of, the secondary vial).

In one embodiment, a pneumatic device is used to control the transfer of a volatile compound, for example, [F-18] fluoropentyne, from the primary reaction pot into a secondary reaction pot. The arms are raised and lowered to facilitate both a) the transfer of activity from the primary reaction pot into the secondary reaction vial and b) the transfer of activity from the secondary reaction vial into the HPLC load vial. Without the pneumatic device or other remotely operated device in place, the raising and lowering of the transfer lines "a" and "b" is performed manually, which requires the operator to intervene during the synthesis resulting in increased radiation exposure to the operator. The transfer lines may be comprised of tubing made out of inert polymeric material, such as PEEK.

In one embodiment, the device may be used to synthesize [F-18]RGD-K5 and [F-18]CP18, [F-18]fluoroethylbromide, [F-18]fluoropropylbromide, [F-18]fluoropropyliodide, [F-18]fluoroDOPA, [F-18]pentyne, [F-18]fluoroethylazide, [F-18]fluorotrimethylsilane, [F-18]fluoropropyne, [F-18] fluoromethyltriflate, [F-18]fluoromethylbromide, [F-18] fluoroethylcholine, [F-18]fluoromethylcholine, [F-18]fluoroacetate, [C-11]acetate, [C-11]-O-Me-tyrosine, [C-11]-methionine and [C-11]choline. K-5 is shown in U.S. Pat. No. 7,666,392, the entirety of which is incorporated by reference herein.

In one embodiment, the device may allow for the transfer of 0.1 to 20 mL of reagents, solvents or crude reaction mixtures into a secondary vial.

Yet, another embodiment as set forth in the present disclosure is directed to a system for labeling. The system has a simple design deemed to be cost-efficient, flexible in adapting to different labeling protocols and have components that do not require cleaning. For example, the platform design should accommodate both traditional labeling protocols requiring both anhydrous and hydrous [F-18]fluoride labeling reaction mixtures.

Yet another embodiment as set forth in the present disclosure is directed to a system that includes the use of several disposable and inexpensive components, obviating the need for complex valves, reagent delivery systems and custom-made glass ware. Excess hardware, such as vacuum pumps, are not necessary for successfully supporting [$^{18}$F]-labeling.

Yet another embodiment as set forth in the present disclosure is directed to a system for synthesizing tracers. The system comprises a source of a solution comprising a radionuclide; a first container comprising a tracer precursor, the first container in communication with the source of solution comprising radionuclide; a second container in communication with the first container, the second container configured to store the tracer; a valve downstream of the source of solution comprising radionuclide and upstream of the first container. The system may further comprise an apparatus configured to separate the radionuclide from the solution. The apparatus is disposed downstream of the source of solution comprising a radionuclide and upstream of the first container. The system may further comprise a third container in communication with the first container. The third container is disposed upstream of the apparatus configured to separate the radionuclide from the solution.

In an embodiment, the third container comprises a plurality of containers connected in series. The third container may be configured to comprise an eluting solvent configured to elute radionuclide from the apparatus configured to separate the radionuclide from the solution. All three containers of the third container may be disposed upstream of the source of solution comprising a radionuclide. In an alternative embodiment, one container may be disposed upstream of the source of solution comprising a radionuclide and two containers are disposed downstream of the source of solution comprising a radionuclide.

In one embodiment, the system includes a third valve downstream of the two containers and downstream of the first container.

In one embodiment, one container comprises an anion eluting solvent in MeCN/H$_2$O. One container may comprise aqueous HCl.

In one embodiment, the system includes an anion exchange cartridge in communication with and downstream of the third container. The system may further comprise a filter in communication with and downstream of the first container. The first container may be configured to comprise MeCN.

In one embodiment, the system includes a gas source in communication with the third container. The gas source is configured to push contents in the three containers toward the first container. The system may further include an apparatus for transferring chemical solution, the apparatus comprising: a first line in communication with the first container, the first line configured to deliver chemical reagents, reaction intermediates and/or reaction products to the first container; and a second line in communication with the first container. The first line and second line are configured to move toward and away from the bottom of the first container.

In one embodiment, the system does not comprise a drying apparatus. At least one component is disposable. In an alternative embodiment, the system may include a drying apparatus in communication with a QMA.

Yet, another embodiment as set forth in the present disclosure is directed to a system for synthesizing tracers, the system comprising: a source of a solution comprising a radionuclide; a first container comprising a tracer precursor, the first container in communication with the source of solution comprising radionuclide; an apparatus configured to separate the radionuclide from the solution, the apparatus being disposed downstream of the source of solution comprising radionuclide and upstream of the first container; and a source of eluting solvent configured to elute radionuclide separated by the apparatus configured to separate the radionuclide from the solution.

In one embodiment, the system includes at least one eluting solvent source, the eluting solvent source being disposed upstream of the apparatus configured to separate the radionuclide from the solution. The system may further include a second valve positioned between the eluting solvent source and the apparatus configured to separate the radionuclide from the solution. The system may further include at least one first valve downstream of the source of a solution comprising a radionuclide and being disposed downstream of the apparatus configured to separate the radionuclide from the solution and upstream of the first container. The system may further include a third container in communication with the first container. The third container is disposed upstream of the apparatus configured to separate the radionuclide from the solution.

In one embodiment, the third container is the source of eluting solvent. The source of eluting solvent further comprises aqueous HCl.

In one embodiment, the system may further include a heat source in communication with the first container. The first container comprises tracer precursor. The system may further include a lead shield. The system may further include an apparatus for transferring chemical solution, the apparatus comprising: a first line in communication with the first container, the first line configured to deliver chemical reagents, reaction intermediates and/or reaction products to the first container; and a second line in communication with the first container. The first line and second line are configured to move toward and away from the bottom of the first container.

In one embodiment, the system further comprises a gas source in communication with the third container. The system may further include an anion exchange apparatus downstream of the first container and upstream of the second container. The system may further include a second container in communication with the first container, the second container configured to store the tracer.

The above and other various embodiments as set forth in the present disclosure will be more apparent from the following detailed description of embodiments taken in conjunction with the accompanying drawings.

BRIEF DESCRIPTION OF THE DRAWINGS

The following detailed description, given by way of example, but not intended to limit the disclosure solely to the specific embodiments described, may best be understood in conjunction with the accompanying drawings, in which.

DETAILED DESCRIPTION

Below, the embodiments as set forth in the present disclosure which is disclosed here will be described with reference to the diagrams. Reference will now be made in detail to various embodiments of the disclosure, one or more examples of which are illustrated in the accompanying drawings. Each example is provided by way of explanation of the disclosure and is in no way limiting the present disclosure.

Figure 1:
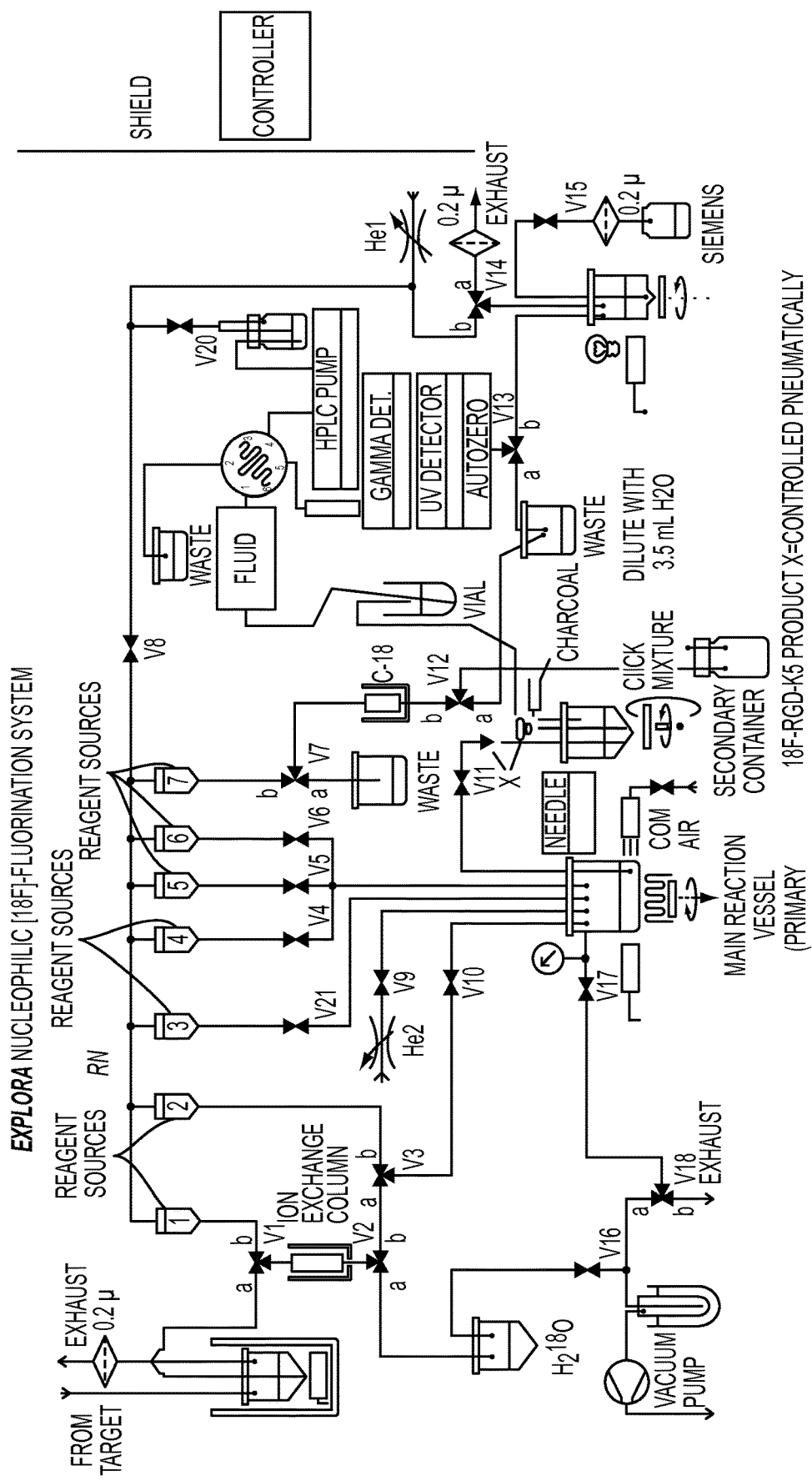
FIG. 1 shows a system according to one embodiment as set forth in the present disclosure that may be used to synthesize various chemicals including $^{18}$F-fluoropentyne, via click labeling with an RGD-K5 precursor.

FIG. 1 shows a schematic of a system according to an embodiment as set forth in the present disclosure. Part of the system may be a module with or without hardware and/or software. In the embodiment shown in FIG. 1, the module, Explora RN from Synthra GmbH is used. Other modules may also be used.

In addition, the system may be on a macrofluidic or microfluidic scale. A "microfluidic device" or "microfluidic chip" is a unit or device that permits the manipulation and transfer of small amounts of liquid (e.g., microliters or nanoliters) into a substrate comprising micro-channels and micro-compartments. The microfluidic device may be configured to allow the manipulation of liquids, including reagents and solvents, to be transferred or conveyed within the micro-channels and reaction chamber using mechanical or non-mechanical pumps. Microfluidic devices permit manipulation of extremely small volumes of liquid, for example on the order of about 1 mL to about 1 μL. In a microfluidic system, the containers (such as the vials) may contain a volume of about 5 μL to about 1,000 μL. In a macrofluidic device, the volumes are greater. In the present disclosure, the containers may hold at least 1 mL; more specifically, about 1 mL to about 50 mL, depending on the synthesis. In some embodiments, the containers may hold up to about 10 mL.

The system may comprise at least one reagent source. The system in FIG. 1 comprises at least seven reagents sources (1, 2, 3, 4, 5, 6, and 7). These may include any suitable reagent. In the embodiment shown, the reagents are those used to synthesize radioactive molecules that may be used for PET or SPECT imaging. As such, the reagent sources may comprise aqueous $K_2CO_3$, aqueous $KHCO_3$, aqueous tetrabutyl ammonium bicarbonate, Kryptofix™ K222, MeCN, HCl, $H_2O$, etc.

The general operation of a microfluidic chip, such as that shown in PCT/US2008/060267 may be as follows. First, target water ($H_2^{18}O$ and radionuclide) is passed through an ion exchange cartridge, also referred to as an ion exchange column, to trap F-18 out of a dilute solution. $K_2CO_3$ may then be released into a concentrated solution that enters the reactor, also referred to herein as a primary container. Next, K222/MeCN solution may be delivered. After the reagents have mixed, nitrogen may be delivered. Solvents evaporate quickly leaving behind a residue containing an F-18 KF/K222 complex. Next, the precursor (such as mannose triflate) may be delivered to the reactor.

The resulting reaction mixture may be heated, allowing it to boil for a few seconds to achieve adequate mixing. The residue is usually then re-dissolved. Next, the reaction mixture may be superheated to about 140° C. After cooling, the solvent is evaporated by the flow of nitrogen. Deprotection is then carried out by introducing deprotection agents such as ethanolic HCl into the reactor. Once again, the reaction mixture may be heated. Then, the solvents may be evaporated, leaving behind a residue of FDG. The final step of product elution takes place when solvents such as water enters the reactor from one channel and carries the products out of another channel.

The reagents from the reagent sources are fed to a reactor such as the primary container or Main Reaction Vessel via a plurality of lines, which may or may not be regulated by valves (see e.g., V21, V4, V5, V6, etc.). The primary container is configured to contain these reagents and, possibly, facilitate a chemical reaction within the primary container. The container may hold about 0.1 to about 10 mL of radioactive evaporate. As such, the primary container is configured to contain a chemical solution, which may comprise chemical reagents, reaction intermediates and/or reaction products; the container may also facilitate reactions. In one embodiment explained in more detail below, the primary container contains an alkyne with a good leaving group, $^{18}$F-fluoride, Kryptofix™ 2.2.2, $K_2CO_3$ and MeCN. These reagents may be reacted with optional heat and/or stirring via first heat source and/or stir bar and polarized source, etc.

As shown in FIG. 1, also in communication with the primary container is a pressure source (COM AIR). The pressure source may provide pressurized gas or liquid to the system. In the embodiment shown in FIG. 1, the pressure source provides gas to the primary container.

In communication with the primary reaction container is a first line, which is also in communication with a secondary container via valve V11. In the embodiment shown, this is labeled as "Click Mixture" but other reactions may be carried out in this container. The secondary container is configured to contain a chemical solution such as chemical reagents, reaction intermediates and/or reaction products. The system may also comprise a heat source and/or stirrers adjacent to or within the secondary container. In the system shown in FIG. 1, the secondary container comprises a click chemistry mixture. The container may hold about 0.1 to about 10 mL of radioactive evaporate. Such a click chemistry mixture may be the result of a reaction of the alkyne with a good leaving group, $^{18}$F-fluoride, Kryptofix™ 2.2.2, $K_2CO_3$ and MeCN of the primary container. In other embodiments, other click chemistry reaction products or intermediates may be contained in the secondary container.

As shown in FIG. 1, the primary container may be in communication with the secondary container via the first line. In one embodiment, the communication takes place via distillation. In other words, the products and/or intermediates in the primary reaction container are distilled to the secondary container. Further, the system may comprise a valve (V11) downstream of the primary container and upstream of the secondary container. As shown in FIG. 1, the valve regulates flow through the first line. Also in communication with the secondary container is a second line configured to transport chemical reagents, reaction intermediates and/or products and/or gas. As described in more detail below, the first and second lines are configured to move within the secondary container. These lines may move in unison or independently of one another. In an embodiment, the first line and the second line may be controlled pneumatically through two arms (shown as element X in FIG. 1)

Various apparatuses may be in communication with the secondary container. Such apparatuses may be an HPLC column, radioactivity detectors, ultraviolet detectors (UV), electrochemical and light scattering-detectors, waste containers, reformulation unit, vacuum pump, etc. Preferably, these are in communication with the secondary vessel via the second line.

As shown in FIG. 1, the system may comprise other components that are known in the art. These may include waste containers, HPLC pumps, UV detectors, etc. Further, the system may be operated manually and/or by a non-transitory computer system or controller. The computer system may include various controllers, hardware and software components as known in the art. Methods of carrying out reactions in the system and operating the remote transfer device may be executed by a computer program. Programs may be stored on an electronic media (electronic memory, RAM, ROM, EEPROM) or programmed as computer code (e.g., source code, object code or any suitable programming language) to be executed by one or more processors operating in conjunction with one or more electronic storage media. The computer system or controller is separated from the other components of the system by a large lead shield. The computer systems, controllers, shielding, hot cells, etc. may be similar to those shown in U.S. patent application Ser. No. 12/803,862, which is incorporated by reference.

The computer may include a processing device, a system memory, a system bus coupling the system memory to the processing device, a storage device, such as a hard disk drive, a magnetic disk drive, e.g., to read from or write to a removable magnetic disk, and an optical disk drive, e.g., for reading a CD-ROM disk or to read from or write to other optical media. The storage device may be connected to the system bus by a storage device interface, such as a hard disk drive interface, a magnetic disk drive interface and an optical drive interface. Although this description of computer-readable media refers to a hard disk, a removable magnetic disk and a CD-ROM disk, it should be appreciated that other types of media that are readable by a computer system and that are suitable to the desired end purpose may be used, such as magnetic cassettes, flash memory cards, digital video disks, etc.

The computer is in electronic communication with the chemical system or microfluidic or macrofluidic reactor. "In electronic communication" means that the computer is physically (e.g., wired) or wirelessly connected to the chemical system and may connected to the reactor directly or via other media. Various sensors (e.g., flow sensors, liquid-gas interface sensors, radioactivity sensors, pressure sensors, temperature sensors, and the like) and other apparatus components (e.g., valves, switches, etc.) can be integrated into the chemical system and be in electronic communication with the computer for process control and monitoring purposes.

The computer, or other external input device, may be coupled to a program storage device and to a controller. The controller may be coupled to at least one valve on the synthesis chip, an inert gas delivery source, a temperature control system, a pressure monitor, and/or a vacuum system.

Figure 2A:
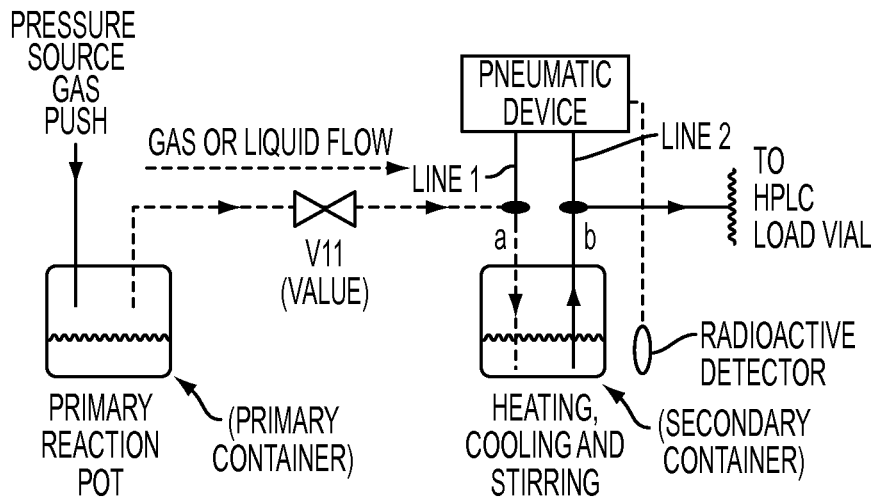
FIG. 2A shows a detailed plan view of the primary container and the secondary container wherein the first line is lowered toward the solution and the second line is positioned farther from the solution.
Figure 2B:
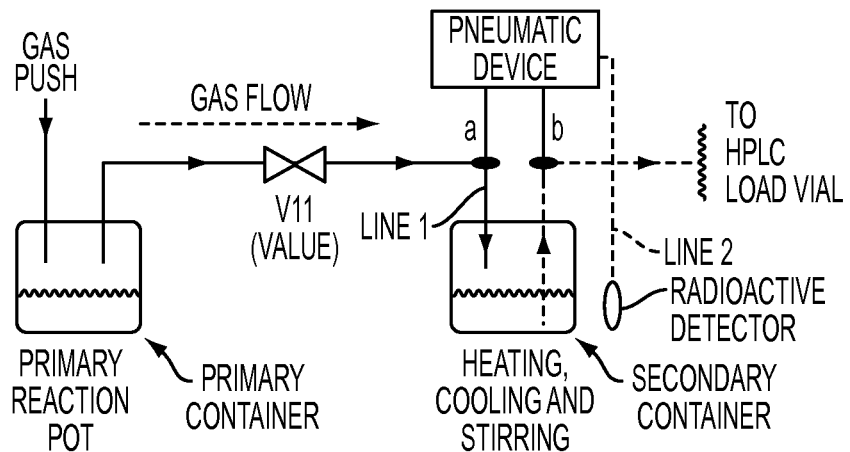
FIG. 2B shows a detailed plan view of the primary container and the secondary container wherein the second line is lowered toward the solution and the first line is positioned farther from the solution.

FIGS. 2A-2B shows the interaction of the primary container and the secondary container in more detail. FIG. 2A shows a transfer of chemical solutions from a primary container to a secondary container. FIG. 2B shows a transfer of chemical solutions from a second container to other units.

As provided above, the first line and the second line are in communication with the secondary container. In particular, at least a portion of each line may be within an interior of the container. Preferably, one of the lines is positioned closer to the bottom of the secondary container than the other line. The "bottom" may change depending on the orientation of the container. As shown, the apparatus and the container are upright; or substantially perpendicular to a ground plane. In the present disclosure, an "in" position indicates where a line is in contact with the chemical solution, and an "out" position indicates where a line is out of contact with the chemical solution In the embodiment shown in FIG. 2A, the first line is positioned closer to the bottom than the second line. In some embodiments, the secondary container is empty. In other embodiments, such as shown in FIG. 2A, it contains reagents, products, intermediates, etc. In the latter situation, the first line may be in communication with or in the reagents, products, or intermediates and the second line may be out of communication with the reagents, products or intermediates. In other embodiments, either line may be outside of the container entirely.

As explained in more detail below, the first line and the second line may be moved by different means. These means include mechanical means, pneumatic means, solenoids, hydraulics, and electronic means that may be controlled by a controller in communication with a computer, etc. Preferably, these means do not require direct operator intervention so as to limit or eliminate user exposure to radiation. Because the unit as set forth in the present disclosure is controlled remotely behind leaded shielding, the operator is protected from radioactive exposure.

A pressure source may provide gas pressure to the primary container. When the primary container contains chemical reagents, reaction intermediates and/or products, etc. gas may be supplied to the primary container. The pressurized gas causes the reagents, products and/or intermediates in the primary container to be moved through the first line and, if the valve 11 is open; to the secondary container. Because the second line is not in communication with the reagents, products, intermediates, etc. (raised above the level of the solution), none of the contents in the secondary vial are transferred out of the secondary container, for example, into the HPLC load vial.

After the gas push is completed, the gas flow may be stopped or reduced by closing the controlling valve (V11). The contents of the secondary vial may now be left to react at various temperatures and times. The contents may optionally be agitated via stirring, heated or cooled or pressurized. If the pneumatic device controls a radioactivity detector, the amount of radioactivity in the secondary vial may be monitored when the radioactivity detector is moved within the proximity of the second container.

The distillation is controlled through the use of valve V11 into a vial containing the reagents for the click reaction ("click mixture"). Once the contents have been successfully transferred and the reaction in the secondary container (e.g., intermediate reaction) is completed, the materials from the secondary vial can be transferred out to another apparatus such as another vial, an HPLC load vial, etc. The chemical materials may be moved by moving the second line closer to the bottom of the reaction vessel; i.e., toward the reagents, products, etc., and moving the first line away from the bottom of the reaction vessel; i.e., away from the reagents, products, etc. Where a click reaction takes place, after distillation and coupling in the presence of Cu(I) in the secondary vial, the crude material may be purified by semi-preparative HPLC.

The valve may be opened such as to allow gas through the first line. This drives the reagents, products, etc. in the secondary container through the second line and out of the secondary container. The dotted line shows an actual transferring path of the reagents, products, etc.

In one embodiment, this process undergoes several iterations. In particular, the first line may be moved back toward and into the solution, and the second line may be moved away from the solution. Further, the lines may be moved in different sequences. For example, it may be desirable to transfer material from the primary reaction vial into the secondary reaction vial while both lines are raised above the solution. The lines may be the same distance from the bottom of the container or they may be at different distances. In another embodiment, it may be desirable to have both lines lowered and within the solution, during the transfer of material from the secondary vial to the HPLC load vial.

As provided above, different means may be used for moving the first line and the second line. An example of such an apparatus is shown in FIGS. 3A-3C.

Figure 3A:
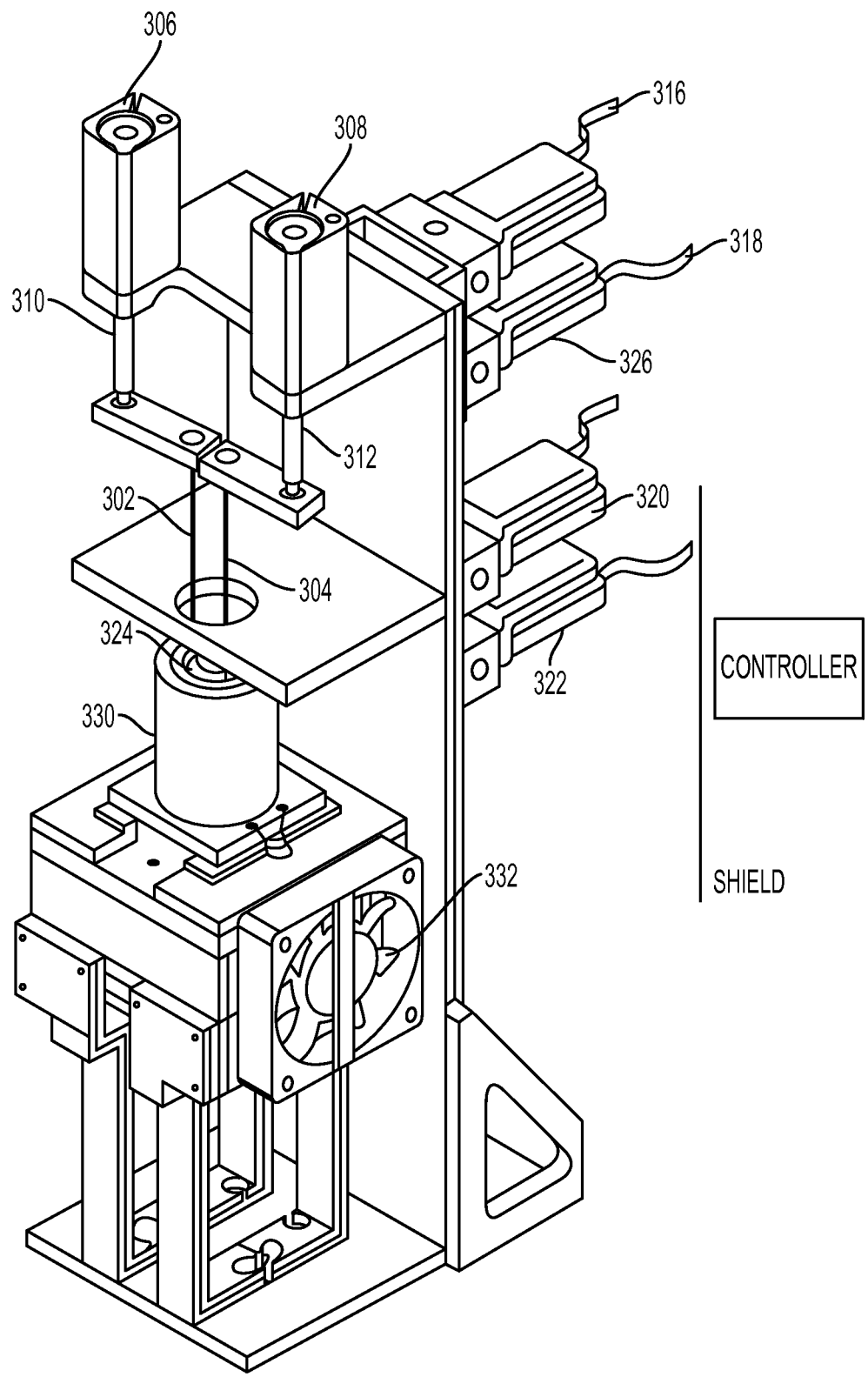
FIG. 3A shows a perspective view of an apparatus for transferring reagent, according to an embodiment as set forth in the present disclosure.
Figure 3B:
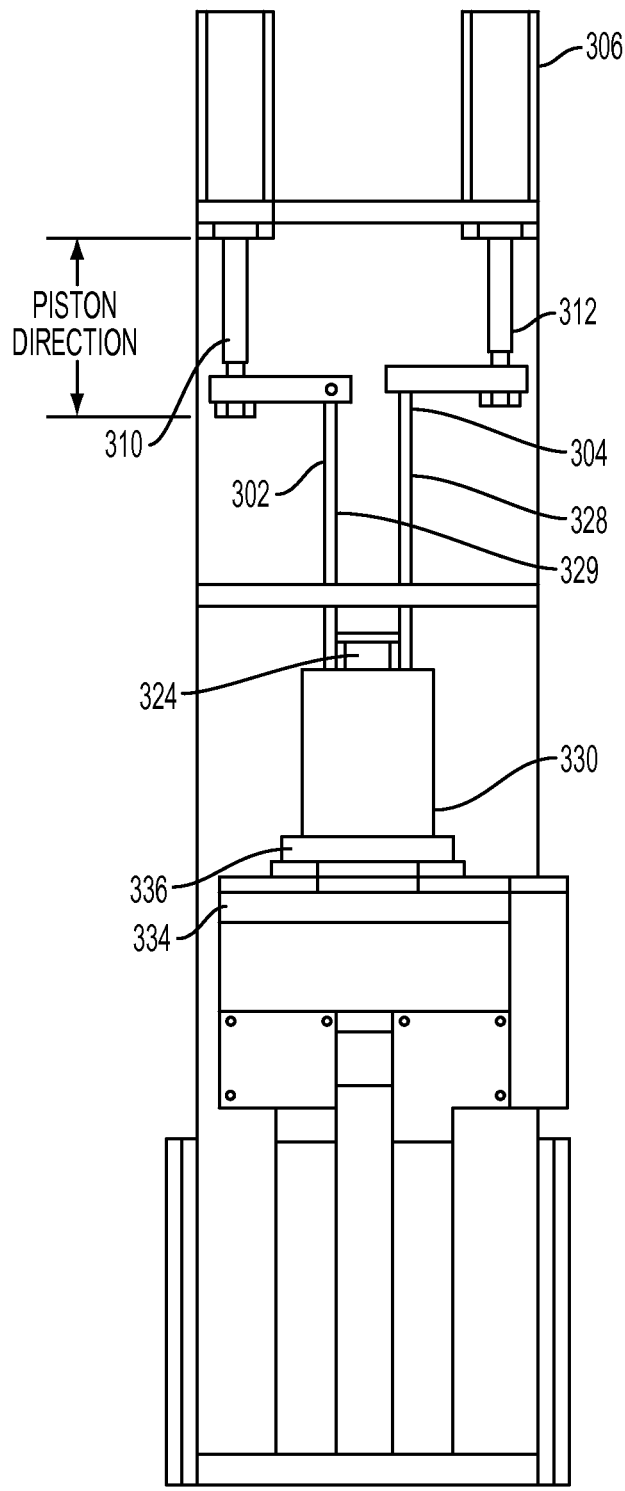
FIG. 3B shows an apparatus for transferring reagent, according to an embodiment as set forth in the present disclosure.
Figure 3C:
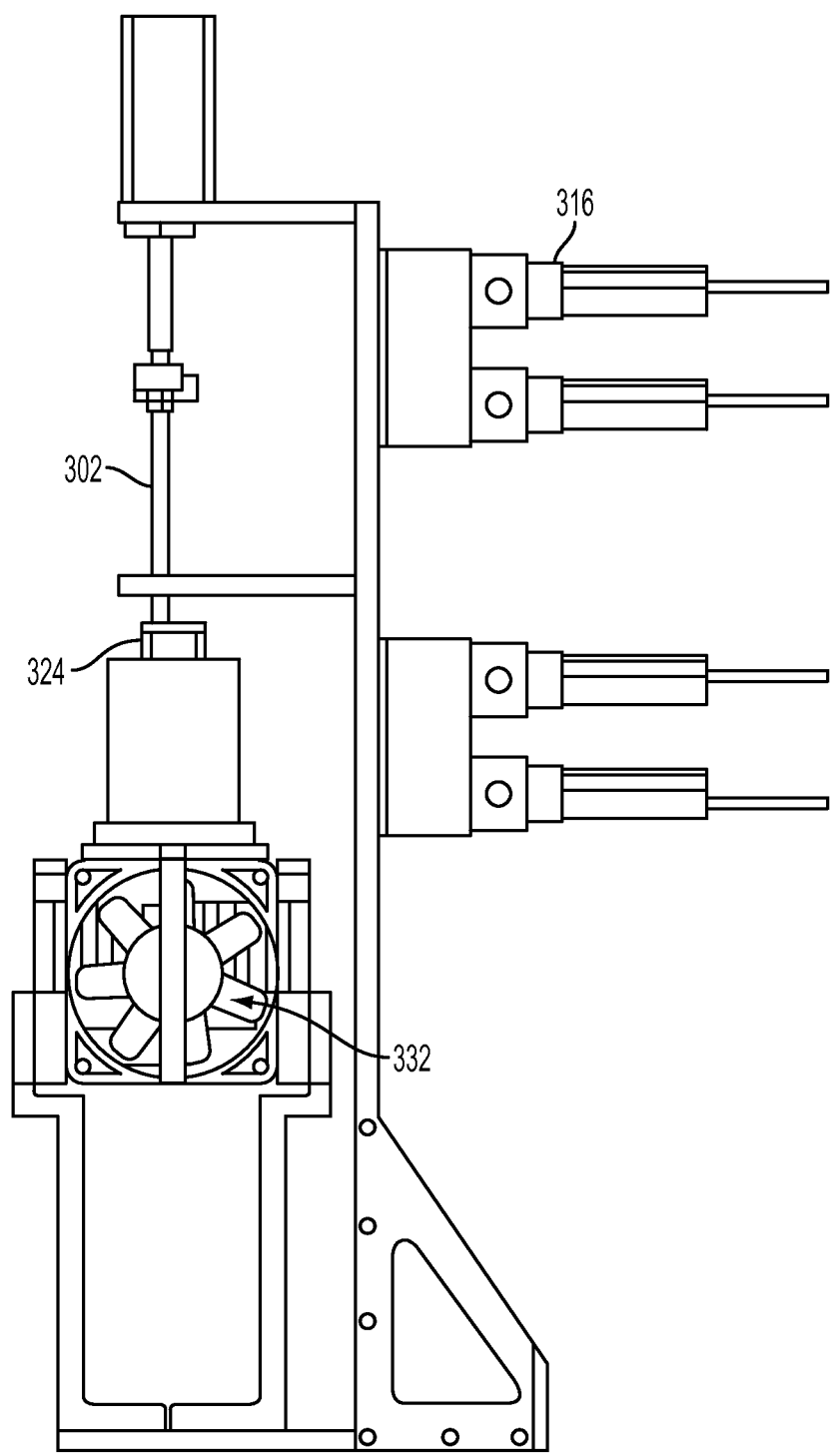
FIG. 3C shows a side plan view of an apparatus for transferring reagent, according to an embodiment as set forth in the present disclosure.

In one embodiment, shown in FIGS. 3A-3C, the first line 302 and the second line 304 are moved by a pneumatic device. The pneumatic device may comprise pneumatic arms including pneumatic actuators 306, 308 coupled to pneumatic pistons 310, 312, which are coupled to the first line 302 and the second line 304. The first line 302 and the second line 304 may be made of a polymer such as PEEK, which are attached to needles 328 that may be made of metal such as stainless steel. A plurality of pneumatic or air valves 316, 318, 320 and 322 are coupled to the pneumatic actuators 306, 308. The system may also comprise a compressor (not shown in FIGS. 3A-C), air dryer (not shown in FIGS. 3A-C), regulators (not shown in FIGS. 3A-C), vacuums (not shown in FIGS. 3A-C), etc. The vial 324 connected to the pneumatic device has a seal that is punctured by tubes such as two needles 328, 329, which are moved up and down by the pneumatic arms. The vial 324 may be protected by a holder 330 such as a PEEK vial holder. Tubes are needed in order to allow for changes in pressure and materials transfer. The tubes themselves could be needles or tubing. The materials could be metal or polymeric. The tubes must be stiff enough to be moved up and down by the pneumatic arms. A detailed view of one embodiment of the lines, needles, etc. and the secondary container is shown in FIG. 3B. Here, the system may comprise at least one charcoal trap or other separation device.

These components may be controlled by a controller. The controller may be a relay logic circuit, programmable controller, air logic or a computer. Regardless, the means used to move the lines may be automated or via a human operator. If the lines are automated, sensors may be required. In one embodiment, the system includes a computer that controls a controller that in turn, controls the movement of the lines. In one embodiment, the system comprises a non-transitory computer-readable medium storing a program that when executed moves the lines. The computer may comprise at least one computer program that may be stored on an electronic media (electronic memory, RAM, ROM, EEPROM) or programmed as computer code (e.g., source code, object code or any suitable programming language) to be executed by one or more processors operating in conjunction with one or more electronic storage media.

As shown in FIGS. 3A-C, the secondary container may be within a container or vial holder 330, which may be a part of a stand or other means for positioning and holding the secondary container at various angles. The stand may comprise a heating element 336, stirrer 334, cooling fan 332, etc. As shown in FIGS. 3A-C, the secondary container, also referred to as vial 324, is disposed perpendicular with respect to the ground plane and the first and second lines move vertically (or perpendicularly) to the ground plane. It will be appreciated that the secondary container may be positioned differently. For example, it may be horizontally disposed wherein the lines are vertical or horizontal.

Figure 4:
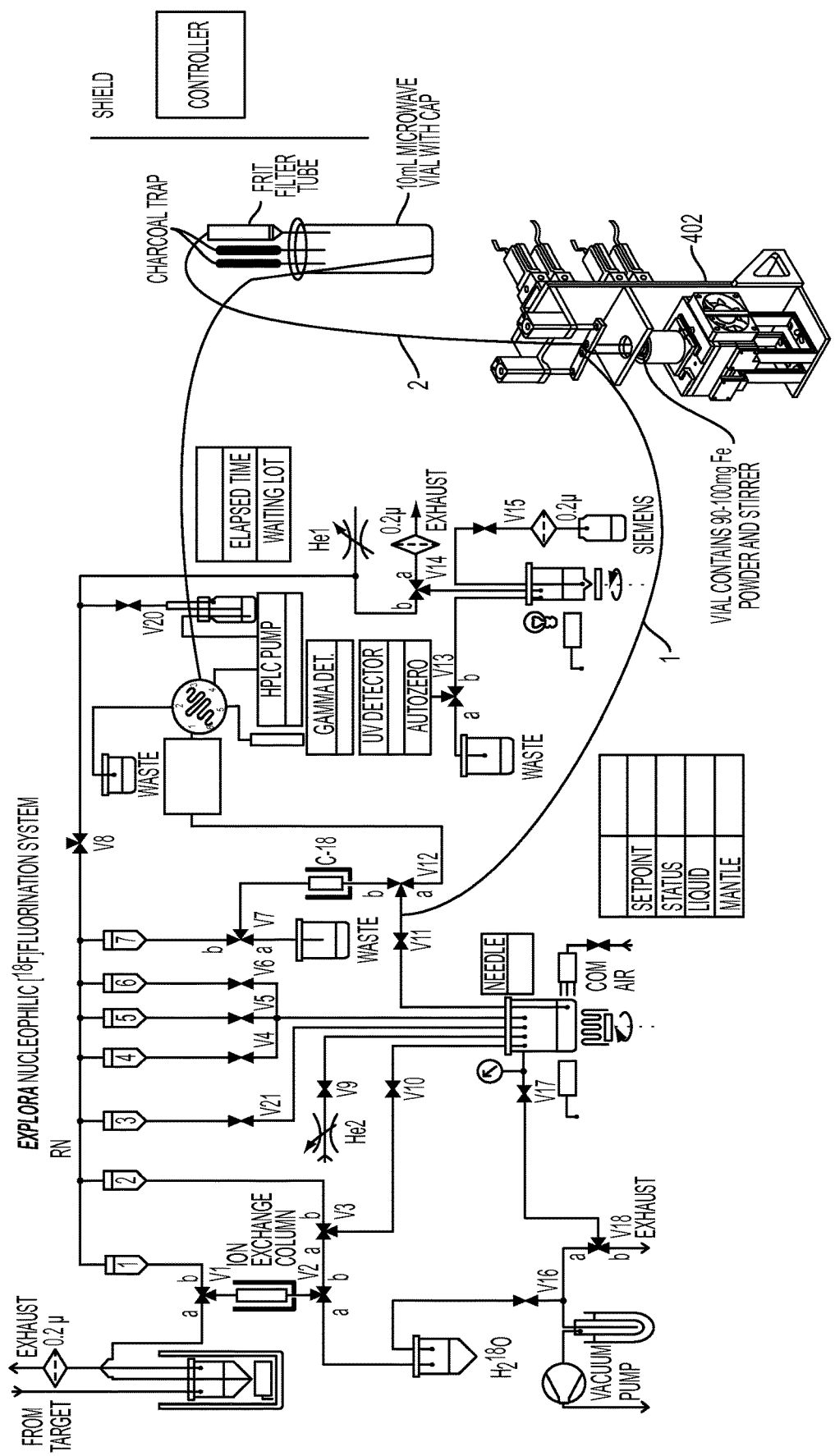
FIG. 4 shows a system and apparatus according to an embodiment invention set forth in the present disclosure. This system may be used for synthesizing the compound T807 as well as others.

FIG. 4 shows a system and apparatus according to an embodiment invention set forth in the present disclosure. The system in FIG. 4 includes similar components with that in FIG. 1. But, the secondary container in FIG. 4 is shown by an exemplary implementation 402, similar with that in FIGS. 3A-C. The reference numerals 1 and 2 in FIG. 4 represent line 1 and line 2 in communication with the secondary container respectively. This system may be used for synthesizing the compound T807 as well as others The device, system and method are also useful for the capture of other volatile radiolabeled intermediates or tracers in addition to [F-18]fluoropentyne. Radiolabeled distillates that may be isolated using this device are shown in Table 1. Oftentimes, these radiolabeled intermediates may be converted into much more elaborate radiotracers.

TABLE 1

Table of labeled intermediates that can be prepared using the remote transfer device, system and method.

| Labeled intermediate | Tracer |
| --- | --- |
| [F-18]fluoropentyne | RGD-K5 |
| [F-18]fluoropentyne | CP18 |
| [F-18]fluoroethylbromide | N, S, or O-alkylated tracers (eg fluoroethyltyrosine) |
| [F-18]fluoroethylbromide | N, S, or O-alkylated tracers (eg fluoroethylcholine) |
| [F-18]fluoromethylbromide | N, S, or O-alkylated tracers (eg fluoromethylcholine) |
| [F-18]fluoromethyltriflate | N, S, or O-alkylated tracers (eg fluoromethylcholine) |
| [F-18]fluoropropylbromide | N, S, or O-alkylated tracers |
| [F-18]fluoropropyliodide | fluoropropyl-labeled tracers |
| [F-18]fluoroethylazide | RGD-labeled tracers fluorotrimethylsilane |
| [F-18]fluorotrimethylsilane | or [F-18]F-1,2,3-triazole containing tracers (eg. |
| [F-18]fluoropropyne | RGD-K5) |
| [F-18]fluoroacetate | [F-18]fluoroacetate |
| [F-18]T807 | [F-18]T807 |
| [C-11]methyliodide | [C-11]-O—Me-tyrosine |
| [C-11]methyliodide | [C-11]-methionine |
| [C-11]methyliodide | [C-11]choline |
| [C-11]methylbromide | [C-11]-O—Me-tyrosine |
| [C-11]methylbromide | [C-11]-methionine |
| [C-11]methylbromide | [C-11]choline |
| [C-11]methyltriflate | [C-11]-O—Me-tyrosine |
| [C-11]methyltriflate | [C-11]-methionine |
| [C-11]methyltriflate | [C-11]choline |

Examples

Typical Preparation of [F-18]Fluoride for Labeling:

Aqueous [F-18]fluoride ion produced in the cyclotron target, is passed through an anion exchange resin cartridge. The [O-18]$H_2O$ readily passes through the anion exchange resin while [F-18]fluoride is retained. The [F-18]fluoride is eluted from the column using a solution of potassium carbonate (3 mg) in water (0.4 mL) and is collected in a reaction vessel. Kryptofix™ 222 (20 mg) dissolved in acetonitrile (1 mL) is added to the aqueous [F-18]fluoride in the reaction vessel. The Kryptofix™ sequesters the potassium ions preventing the formation of strong K+/F on-pairs. This increases the chemical reactivity of the [F-18]fluoride ions. The mixture is dried by heating between 68-95° C. under reduced pressure (250 mbar) and a stream of argon. This evaporation step removes the water and converts the [F-18] to an anhydrous complex, which is much more reactive than aqueous [F-18]fluoride.

Synthesis of RGD-K5 Facilitated by the Pneumatic Transfer Device:

$^{18}$F-labeling of RGD-K5 was performed on an automated synthesis module ("Explora RN" from Synthra GmbH) with hardware modifications (cf. FIG. 2) to accommodate the volatility of $^{18}$-fluoropentyne. The main reaction vessel was connected to the click chemistry reaction vial through valve V11. Both lines connected to V11 are pneumatically con- trolled to raise and lower the transfer lines during the distillation process using the device described herein in Scheme 1. The HPLC transfer line, which connects the click chemistry vial to the HPLC load vial, is also pneumatically controlled to facilitate the transfer process.

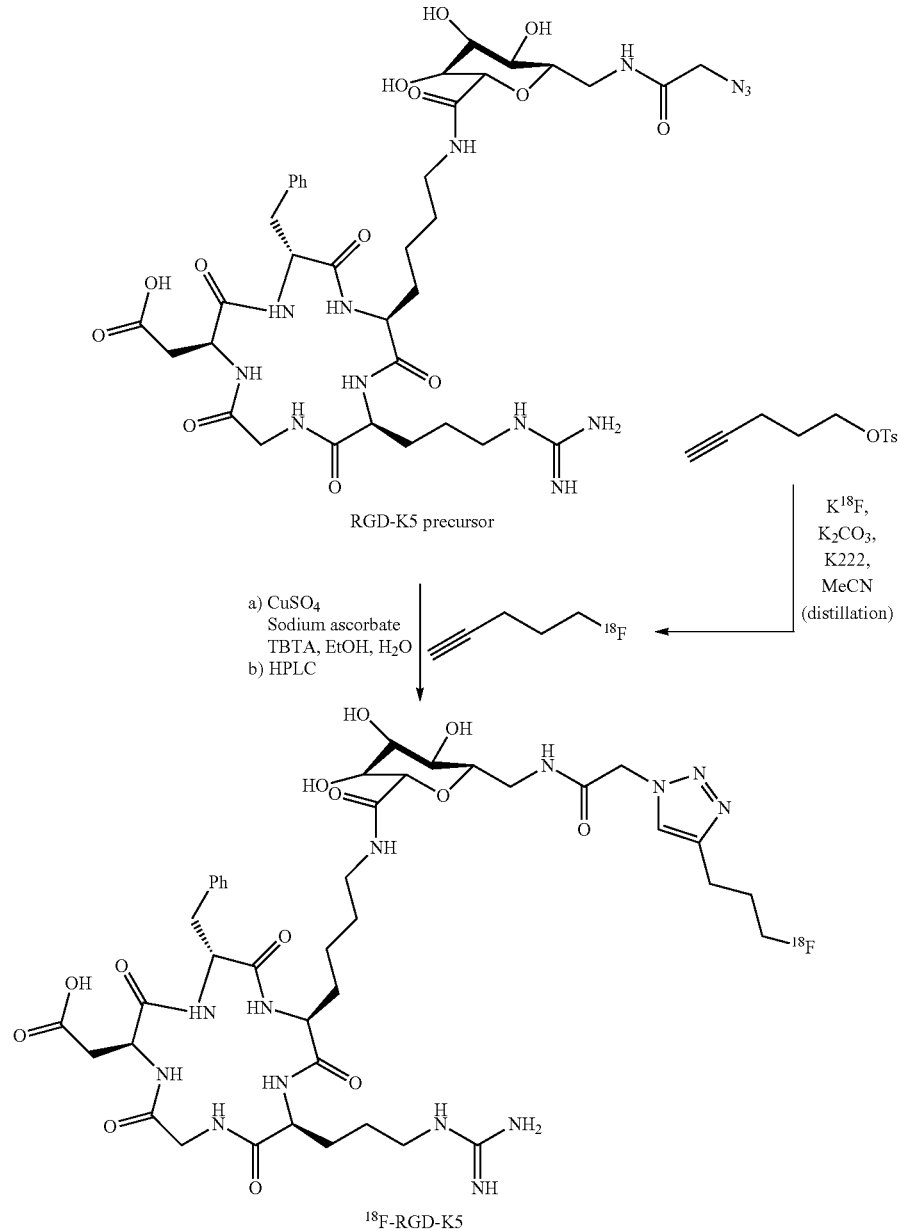

Scheme 1: Synthesis of RGD-K5

Inside the primary reaction vessel, pentyne tosylate (20 mg) was reacted with anhydrous $^{18}$F-fluoride in the presence of Kryptotix™-[2.2.2] (20 mg) and K$_2$CO$_3$ (3 mg) in MeCN (0.4 to 1.0 mL) at 110° C. for 3 min and the resulting $^{18}$F-fluoropentyne was distilled through the connecting valve V11 into the secondary vial for the click reaction ("click mixture" vial) (cf. Scheme 2). The click mixture vial contained the RGD-K5 azide precursor (4 mg), Cu(I) (generated by the in situ reduction of CuSO$_4$ (0.25 mL of a 0.1 M solution) with sodium ascorbate (40 mg)), and tris[(1- benzyl-1H-1,2,3-triazol-4-yl)methyl]amine (TBTA, 15 mg)) in aqueous ethanol/acetonitrile (1:1, 0.5 mL total). A charcoal vent was placed in the click mixture vial to trap the volatile $^{18}$F-fluoropentyne that might be released from the click vial. After reacting for 10 to 30 minutes at room temperature, the transfer lines are pneumatically raised and lowered. The crude reaction mixture was transferred to an intermediate HPLC load vial containing water (4 mL) for dilution prior semi-preparative HPLC purification. After purification of the crude reaction mixture by semi-preparative RP-HPLC (acetonitrile: aqueous trifluoroacetic acid), the product was reformulated via C18 cartridge reconstitution as a solution in a maximum of 10% EtOH:water. The total process time was 90 minutes, i.e. less than one half-life.

Synthesis of CP18 Facilitated by the Pneumatic Transfer Device:

$^{18}$F-labeling of CP-18 was performed on an automated synthesis module ("Explora RN" from Synthra GmbH) with minor hardware modifications (cf. FIG. 2), in order to accommodate the volatility of $^{18}$F-fluoropentyne. CP-18 is shown in U.S. Ser. No. 12/433,211, which is incorporated by reference herein. The primary reaction vessel was connected to the click chemistry reaction vial through valve V11. Both lines connected to V11 are pneumatically controlled to raise and lower the transfer lines during the distillation process using the device described herein in Scheme 1. The HPLC transfer line, which connects the click chemistry vial to the HPLC load vial, is also pneumatically controlled to facilitate the transfer process.

aqueous ethanol/acetonitrile (1:1, 0.5 mL total). A charcoal vent was placed in the click mixture vial to trap the volatile $^{18}$F-fluoropentyne that might be released from the click vial. After reacting for 10 to 30 minutes at room temperature, the transfer lines are pneumatically raised and lowered. The crude reaction mixture was transferred to an intermediate HPLC load vial containing water (4 mL) for dilution prior semi-preparative HPLC purification. After purification of the crude reaction mixture by semi-preparative RP-HPLC (acetonitrile: aqueous formic acid), the product was reformulated via C18 cartridge reconstitution as a solution in a maximum of 10% EtOH:water. The total process time was 90 minutes, i.e. less than one half-life.

Synthesis of T807:

A solution of the precursor, (T807P, 1.0 mg) dissolved in anhydrous DMSO (0.5±0.1 mL) is added to the reaction vessel containing the anhydrous [F-18]Fluoride. The vessel is heated to 100° C. for 10 minutes to induce displacement of the —NO$_2$ leaving group by [F-18]fluoride. The reaction mixture was cooled to 50° C., the crude reaction mixture is pushed into a secondary vial, attached to the pneumatic device, through V11 (FIG. 4, line 1) containing Fe powder (90-100 mg), followed by 1.0 mL of formic acid (99% purity). The reaction mixture is heated to 100° C. for 15 minutes, then cooled to 50° C. At this point water is added (3.5 mL) and the contents are pushed through the needle, via Scheme 2: Synthesis of CP18.

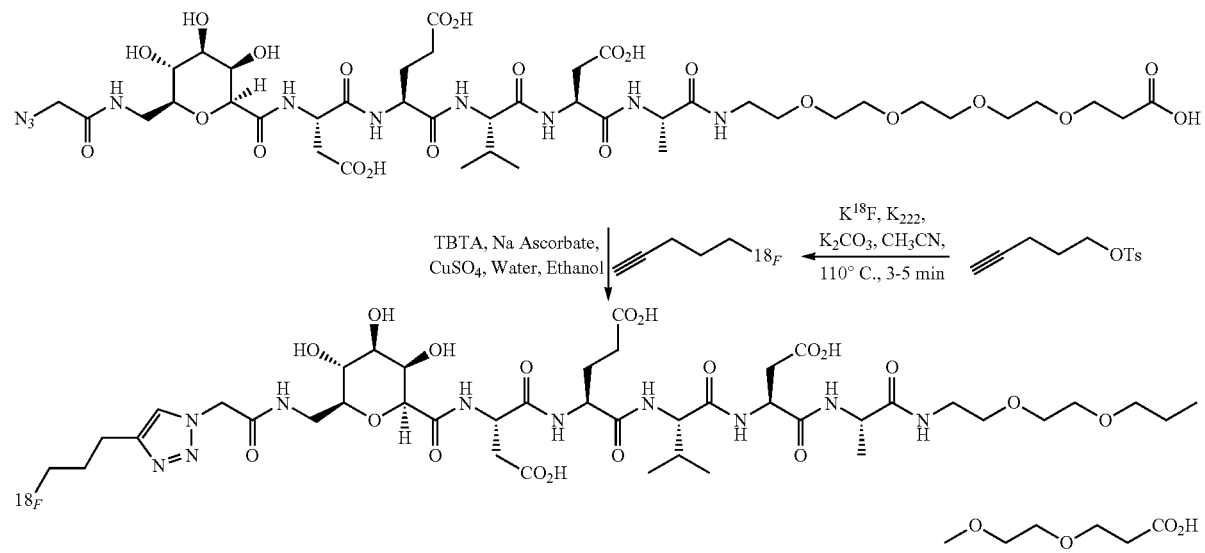

Inside the reaction vessel, pentyne tosylate (20 mg) was reacted with anhydrous $^{18}$F-fluoride in the presence of Kryptofix™-[2.2.2] (20 mg) and K$_2$CO$_3$ (3 mg) in MeCN (0.4 to 1.0 mL) at 110° C. for 3 min and the resulting $^{18}$F-fluoropentyne was distilled through the connecting valve V11 into the collection vial for the click reaction ("click mixture" vial) (cf. Scheme 3). The click mixture vial contained the CP18 azide precursor (4 mg), Cu(I) (generated by the in situ reduction of CuSO$_4$ (0.25 mL of a 0.1 M solution) with sodium ascorbate (20 mg)), and tris[(1-benzyl-1H-1,2,3-triazol-4-yl)methyl]amine (TBTA, 7.5 mg)) in the pneumatic device, through a filter (FIG. 4, line 2) into a third vial (HPLC load vial). The reaction mixture containing crude [F-18]T807 is transferred to the HPLC sample loop (5 mL) and purified via chromatographic separation using a semi-preparative HPLC column, with 100% H$_2$O containing 0.1% 12N HCl. After 5 min, the eluent is changed to 18% EtOH: 82% H$_2$O with 0.1% 12N HCl until the product elutes off the column. The column effluent is monitored using UV (254 nm) and radiometric detectors connected in series. The purified [F-18]T807 is collected from the column at the retention time window determined for the T807 reference standard, coinciding with the time that the radiometric detectors begin showing the strong radioactive peak. The collected HPLC fraction is then diluted with 50 mL of sterile water for injection, optionally containing ascorbic acid. The diluted fraction is passed through an activated C-18 cartridge, capturing the product on the cartridge. The cartridge is then washed with water (10 mL), and the product is then eluted off with EtOH (0.5 mL), followed by approximately 21 mM sodium phosphate (4.5 mL). In this particular example, a secondary reactor was needed in order to decompose unreacted precursor. Transferring the material from the secondary reaction pot into the HPLC load vial was added through the use of the pneumatic device. T807 is shown in U.S. Ser. No. 13/035,405, which is incorporated by reference herein.

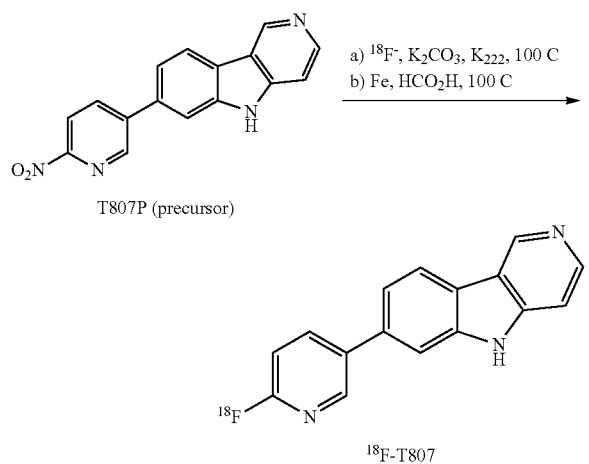

All the above operations have been performed with the use of this remotely operated device from outside the "hot" (exposed to radiation) cell in a shielded environment. This device reliably transfers material from the primary vial to the secondary vial to the HPLC load vial, is easy to operate, has a small footprint and easy to clean for subsequent radiolabeling runs.

Another embodiment as set forth in the present disclosure is directed to an apparatus and system for synthesizing chemical compounds such as tracers. In one embodiment, the apparatus and system may be used to synthesize radiolabeled compounds to be used in imaging; for example, PET or SPECT imaging. The radiolabeled compounds may comprise radionuclides such as $^{11}$C, $^{13}$N, $^{15}$O, and $^{18}$F.

The apparatus and system may be used to synthesize various radiolabeled compounds such as [F-18]FDG, [F-18] NaF [F-18]Fluoro-DOPA (U.S. Pat. No. 7,022,872), [F-18] FLT (U.S. Pat. Nos. 7,160,537 and 7,419,653), [F-18]AV-45 and radiolabeled: HX-4 (see U.S. Pat. No. 7,807,394), K-5 (see U.S. Pat. No. 7,666,392), TA-4 (see U.S. Pat. No. 7,928,210), VM4037a (see U.S. Pat. No. 7,829,063), W372 (see U.S. Ser. No. 12/509,259) T794, T805, T807 (see U.S. Ser. Nos. 12/661,777 and 13/035,405) to name a few. Additional probes are provided below.

The system and apparatus may synthesize radiolabeled chemicals using hydrous and/or anhydrous protocols and does not include excess components for hydrous protocols.

In one embodiment is provided a simplified apparatus for supporting $^{18}$F-labeling that occurs in high yields optionally with precisely controlled amounts of water without the use of a lengthy drying step. If hydrous conditions are employed, a solvent of a predetermined amount of water in at least one organic solvent is used to: a) elute the $^{18}$F-fluoride from an anion exchange resin and b) perform the $^{18}$F labeling, without drying the $^{18}$F-fluoride, in the presence of at least one labeling reagent and at least one phase transfer catalyst.

Any suitable labeling reagents and phase transfer catalysts may be used. Examples of appropriate labeling reagents include, $K_2CO_3$, $KHCO_3$, $Cs_2CO_3$, potassium mesylate, potassium oxylate, and tetrabutylammonium bicarbonate. An example of a suitable phase transfer catalyst includes Kryptofix™ K222. The organic solvent may include a polar aprotic solvent, such as, for example, acetonitrile, dimethyl sulfoxide ("DMSO"), tetrahydrofuran ("THF"), dimethylformamide ("DMF"), N methylpyrrolidone ("NMP"), and dioxane, as well as others. The organic solvent may also include a polar protic solvent, such as, for example, tBuOH and t-amyl alcohol, as well as others.

The amount of water as a percentage of the total solvent may range from about 0.1% to about 2%. Water, for elution from the anion exchange cartridge however, may range from about 0.1% to about 5%. The amount of base (e.g., $K_2CO_3$) may be about 0.1 to about 50 mg/mL. Because the amount of water is controlled by the elution of fluoride, the percentage of water remains the same from run to run, making the radiochemistry more consistent. Also, because the fluorination appears to tolerate the presence of a small range of water, there is no need to dry the fluoride.

As a beneficial consequence of eliminating the drying step, the decomposition of temperature-sensitive reagents such as Kryptofix™ K222 and tetrabutylammonium bicarbonate ("TBAB") are minimized. Additionally, the reactions are completed in a shorter period of time, leading to higher yields and more usable product in-hand. There is less mechanical wear on the instrument, since a portion of mechanical system is no longer used for drying. Unlike losses of radioactivity commonly reported as a consequence of drying $^{18}$F-fluoride, this method would not suffer from this type of radioactivity loss. Lastly, there are fewer chances of labeling failures due to a consistent amount of water always present in every reaction.

Examples of $^{18}$F-labeled PET probes that can be generated by the method as set forth in the present disclosure include, but are not limited to, [$^{18}$F]-fluorothymidine ("FLT), [$^{18}$F]-3-Fluoro-2-(4-((2-nitro-1H-imidazol-1-yl)methyl)-1H-1,2,3-triazol-1-yl)propan-1-ol ("HX4" or "$^{18}$F-HX4"), fluorodeoxythymidine ("FLT"), 1-[$^{18}$F]fluoro-3-(2-nitro-1H-imidazol-1-yl)propan-2-ol ("F-MISO"), [$^{18}$F] fluoroazomycinarabinofuranoside ("FAZA"), 5-[3-($^{18}$F) fluoropropyl]-2,3-dimethoxy-N-{[(2S)-1-(prop-2-en-1-yl) pyrrolidin-2-yl]methyl}benzamide ("Fallypride"), 9-(4-[$^{18}$F]Fluoro-3-hydroxymethylbutyl)guanine ("FHBG"), 9-[(3-[$^{18}$F]-fluoro-1-hydroxy-2-propoxy)methyl]guanine ("FHPG"), ($^{18}$F)fluoroethyl azide, $^{18}$F 4 flurobenzaldehyde, $^{18}$F-4-fluoroethylbenzoate, $^{18}$F-4-fluoromethyl benzoate, and 7-Methoxy-2 (6-[$^{18}$F]fluoropyridin-3-yl)imidazo[2,1-b]-8-pyridinothiazole ("$^{18}$F W372"). Other examples of $^{18}$F-labeled PET probes that can be generated by the method as set forth in the present disclosure include, but are not limited to, 2'-Deoxy-2'-[$^{18}$F]fluoro-5-fluoro-1-β-D-arabinofuranosyluracil ("FFAU"), as well as the compounds listed in the table below:

TABLE
| | |
|---|---|
| 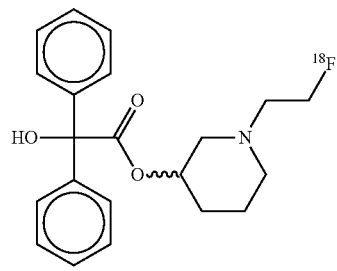 | 1-[2-($^{18}$F)fluoroethyl]piperidin-3-yl hydroxy(diphenyl)acetate |
| 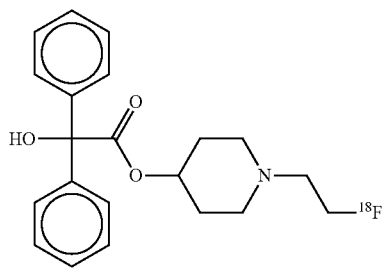 | 1-[2-($^{18}$F)fluoroethyl]piperidin-4-yl hydroxy(diphenyl)acetate |
| 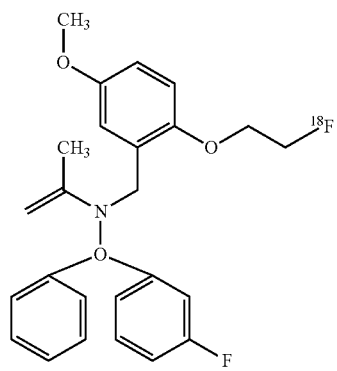 | 1-[2-($^{18}$F)fluoroethyl]piperidin-3-yl hydroxxy(diphenyl)acetate |
| 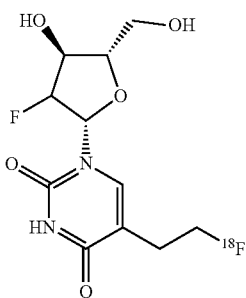 | 1-(2-deoxy-2-fluoro-β-D-arabinofuranosyl)-5-[2-($^{18}$F)fluoroethyl]pyrimidine-2,4(1H,3H)-dione |
| 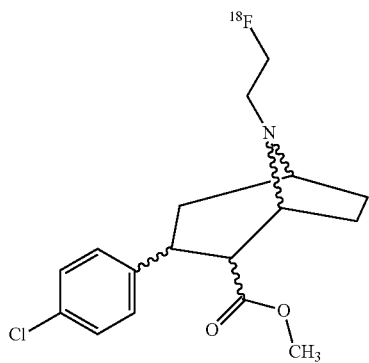 | [$^{18}$F]FECNT 2-Carbomethoxy-3-(4-chlorophenyl)-8-(2-[$^{18}$F]fluoroethyl)nortropane |

TABLE-continued

| | |
|---|---|
| 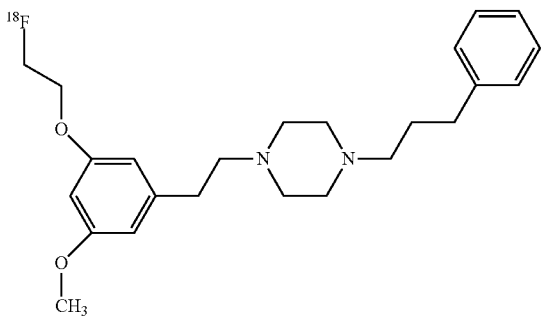 [SMILES: COc1cc(CCN2CCN(CCCc3ccccc3)CC2)cc(OCC[18F])c1] | [18F]Fluoroethyl SA4503<br>1-(2-(4-[18F]-fluoroethoxy-3-methoxyphenyl)ethyl)-4-(3-phenylpropyl)piperazine |
| 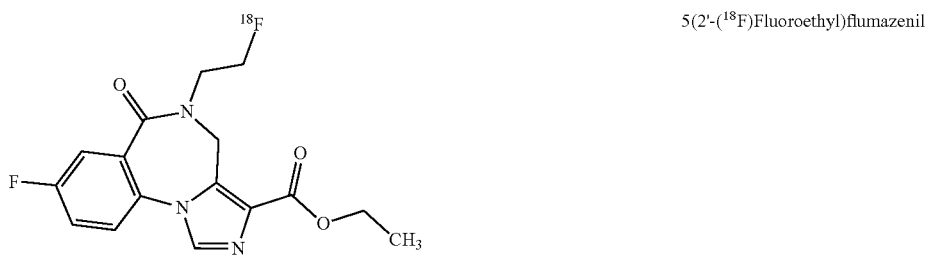 | 5(2'-(18F)Fluoroethyl)flumazenil |
| 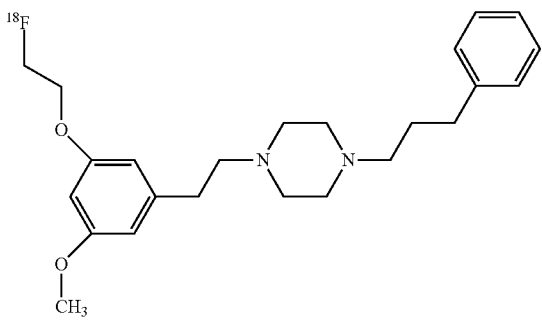 [SMILES: COc1cc(CCN2CCN(CCCc3ccccc3)CC2)cc(OCC[18F])c1] | [18F]Fluoroethyl SA4503<br>1-(2-(4-[18F]-fluoroethoxy-3-methoxyphenyl)ethyl)-4-(3-phenylpropyl)piperazine |
| 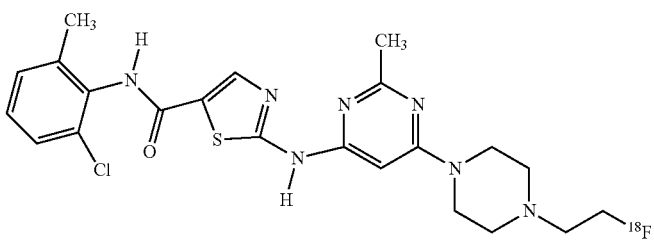 [SMILES: Cc1nc(Nc2ncc(C(=O)Nc3c(C)cccc3Cl)s2)cc(N2CCN(CC[18F])CC2)n1] | N-(2-chloro-6-methylphenyl)-2-[(6-{4-[2-(18F)fluoroethyl]piperazin-1-yl)-2-methylpyrimidin-4-yl)amino]-1,3-thiazole-5-carboxamide |
| 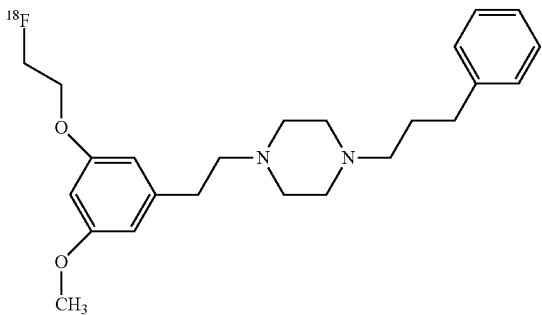 | [18F]Fluoroethyl SA4503<br>1-(2-(4-[18F]-fluoroethoxy-3-methoxyphenyl)ethyl)-4-(3-phenylpropyl)piperazine |

TABLE-continued

| | |
|---|---|
| 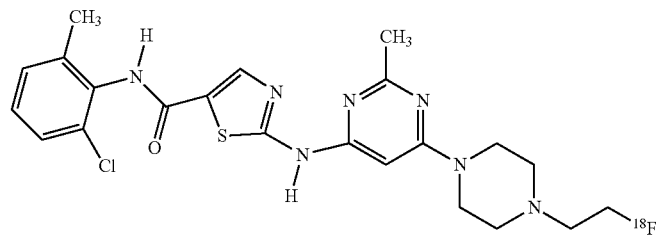 [SMILES: Cc1nc(Nc2ncc(C(=O)Nc3c(C)cccc3Cl)s2)cc(N2CCN(CC[18F])CC2)n1] | N-(2-chloro-6-methylphenyl)-2-[(6-{4-[2-($^{18}$F)fluoroethyl]piperazin-1-yl)-2-methylpyrimidin-4-yl)amino]-1,3-thiazole-5-carboxamide |
| 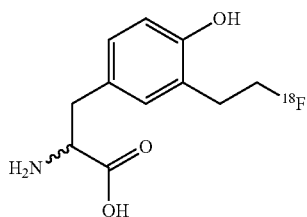 [SMILES: NC(Cc1ccc(O)c(CC[18F])c1)C(=O)O] | 3-[2-($^{18}$F)fluoroethyl]tyrosine |
| 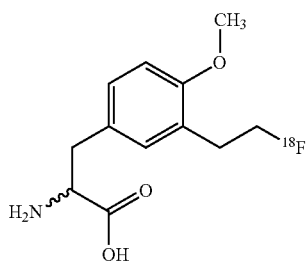 [SMILES: COc1ccc(CC(N)C(=O)O)cc1CC[18F]] | 3-[2-($^{18}$F)fluoroethyl]-O-methyltyrosine |
| 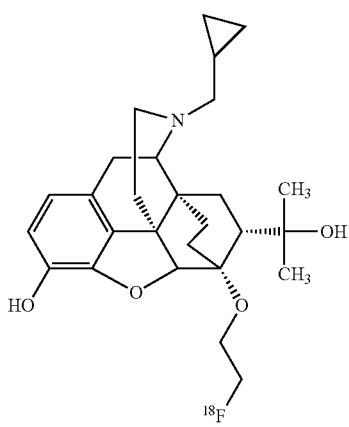 [SMILES: CC(C)(O)[C@H]1C[C@@]23CC[C@]1(OCC[18F])C1Oc4c(O)ccc5c4[C@]12CCN(CC1CC1)C3C5] | [$^{18}$F]FDPN<br>6-O-(2-[$^{18}$F]fluoroethyl-6-O-desmethyldiprenorphine |
| 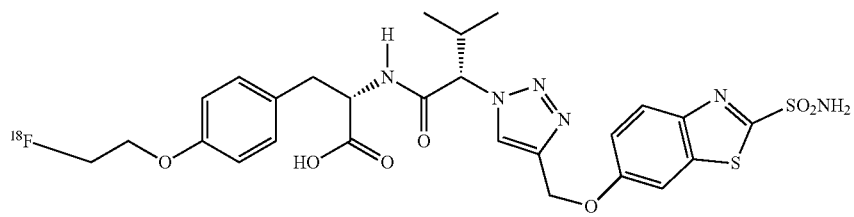VM4037A | [$^{18}$F]VM4-037<br>$^{18}$F-(S)-3-(4-(2-fluoroethoxy)phenyl)-2-(3-methyl-2-(4-((2-sulfamoylbenzo[d]thiazol-6-yloxy)methyl)-1H-1,2,3-triazol-1-yl) butanamido) proanoic acid |

Without intention of being bound by a particular mechanism or theory, the $^{18}$F-fluoride anion may displace a leaving group, which may include, but is not limited to, tosylates, mesylates, triflates, nosylates, brosylates, trialkylammonium salts, sulfonate esters, halogens and nitro-groups with $^{18}$F-fluoride in solvents containing the presence of about 0.1% to about 2.0% water.

In general, the process for generating the $^{18}$F-labeled probe includes loading an amount of $^{18}$F onto an anion exchange cartridge to separate the radionuclide. By anion exchange cartridge, what is meant is any vessel containing any convenient anion exchange resin or other material suitable for adsorbing $^{18}$F. The $^{18}$F loaded on the anion exchange resin is then prepared for elution. This preparation may include washing the cartridge with an organic solvent (e.g., anhydrous acetonitrile) and then drying the cartridge (e.g., by passing an inert gas through the cartridge.)

Next, the $^{18}$F is eluted from the cartridge, for example by passing a solution including water, an organic solvent, a labeling reagent, and a phase transfer catalyst through the cartridge so as to obtain an $^{18}$F solution containing $^{18}$F, water, the organic solvent, the labeling reagent, and the phase transfer catalyst. At this point, the amount of water in the $^{18}$F solution may range from about 0.1% to 5.0%. A probe precursor is then combined with the $^{18}$F solution so as to arrive at an $^{18}$F-labeling solution which has water in an amount of from about 0.1% to 2.0%. This can be accomplished, for example, by diluting either the probe precursor or the $^{18}$F solution, or both, with an appropriate amount of organic solvent. Accordingly, it is possible to generate the $^{18}$F labeling solution without any drying of the eluted $^{18}$F solution.

While the $^{18}$F-labeling solution should contain water in an amount of from 0.1% to 2.0%, it is preferable for the water to be in an amount of from 0.5% to 1.5%, and more preferable for the water to be in an amount of around 1.0%. In an embodiment using drying, the drying apparatus may be comprised of a gas flow through the QMA and out the vent in the reaction chamber.

Figure 5:
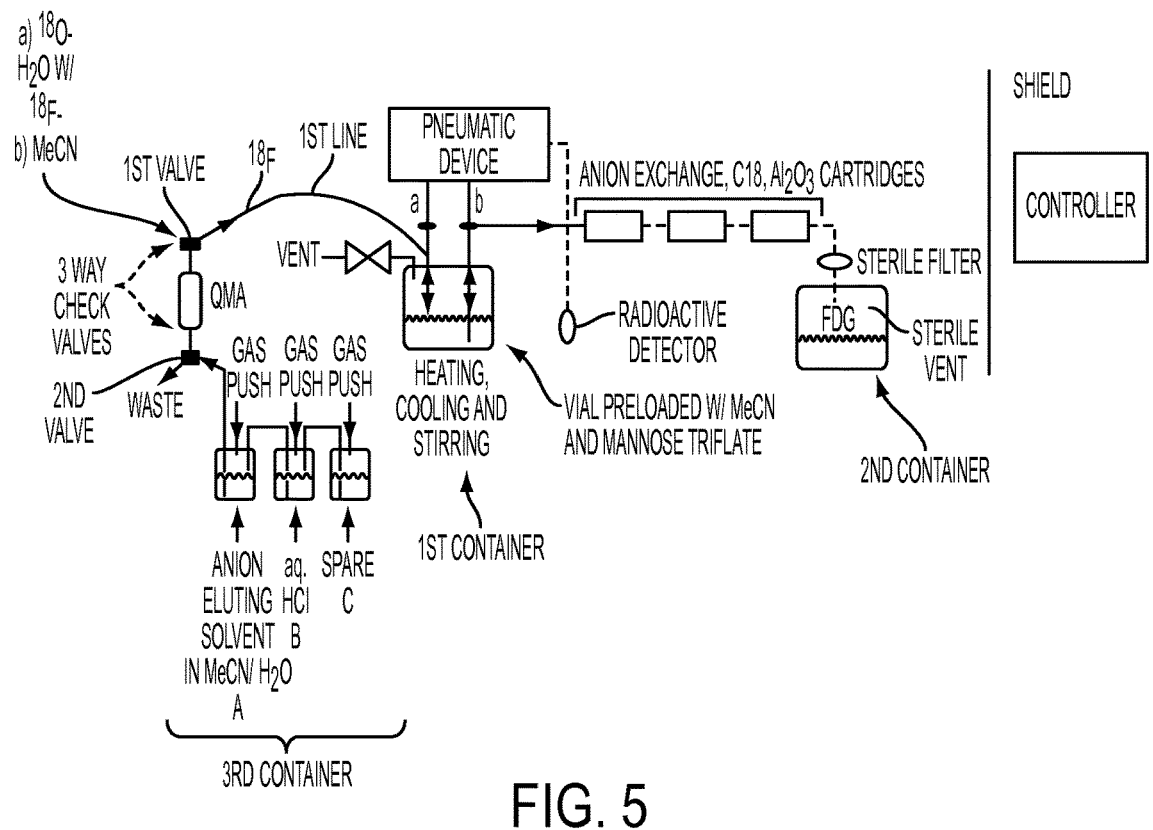
FIG. 5 shows an example of a system for making fluorodeoxyglucose ($^{18}$F) ("FDG" or "$^{18}$F FDG") according to an embodiment as set forth in the present disclosure. This apparatus is capable of supporting labeling methods using both conventional and hydrous solvents for ($^{18}$F)-fluorination.
Figure 6:
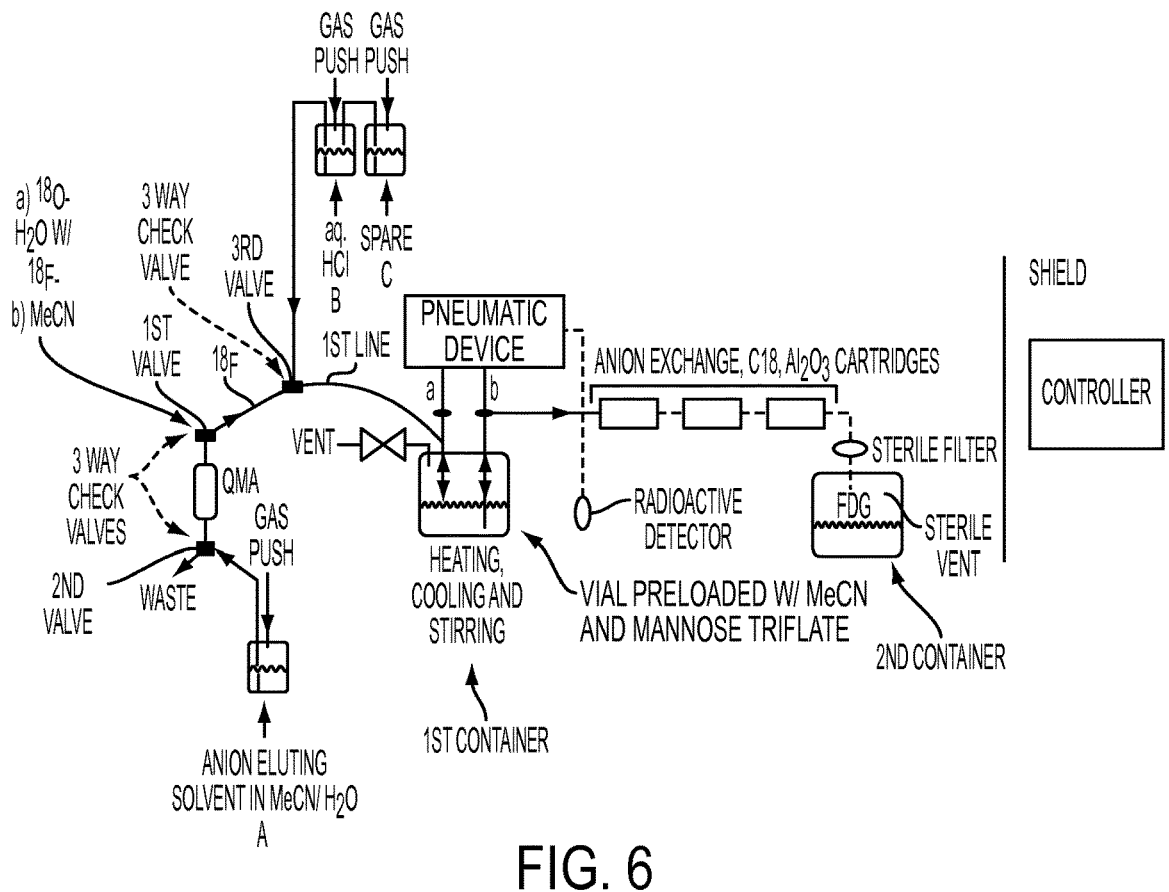
FIG. 6 shows an example of a system for making fluorodeoxyglucose ($^{18}$F) ("FDG" or "$^{18}$F FDG") according to an embodiment as set forth in the present disclosure. This apparatus is capable of supporting labeling methods using both conventional and hydrous solvents for ($^{18}$F)-fluorination.

FIGS. 5 and 6 show embodiments of a system as set forth in the present disclosure for making a radiolabeled tracer. Such a tracer may comprise fluorodeoxyglucose ($^{18}$F) ("FDG" or "$^{18}$F FDG"). These systems can support labeling methods using both conventional and hydrous solvents for ($^{18}$F)-fluorination. It will be understood that the systems of FIGS. 5 and 6 may be used to synthesize various chemical compounds including other radiolabeled tracers. FIGS. 5 and 6 show various components of the system. As explained in more detail below, these components may be contained within various apparatuses. Examples of which are shown in U.S. Ser. Nos. 12/102,822, 12/803,862 and 12/986,323, the entirety of which are incorporated herein by reference. In one embodiment, "hot" (exposed to elevated levels of radiation) components may be in a hot cell, which may be a lead box and "cold" (not exposed to elevated levels of radiation) components may be separate from the hot components.

The systems of FIGS. 5 and 6 may be in electronic communication with and/or operated by a non-transitory computer system optionally having a controller. The computer system or the controller is separated from the other components of the systems by a lead shield (Shield shown in FIGS. 5 and 6). The computer system may include various controllers, hardware and software components as known in the art. Methods of carrying out reactions in the system and operating the remote transfer device may be executed by a computer program. Programs may be stored on an electronic media (electronic memory, RAM, ROM, EEPROM) or programmed as computer code (e.g., source code, object code or any suitable programming language) to be executed by one or more processors operating in conjunction with one or more electronic storage media. The computer systems, controllers, shielding, hot cells, etc. may be similar to those shown in U.S. Ser. No. 12/803,862, the entirety of which is incorporated by reference.

The computer may include a processing device, a system memory, a system bus coupling the system memory to the processing device, a storage device, such as a hard disk drive, a magnetic disk drive, e.g., to read from or write to a removable magnetic disk, and an optical disk drive, e.g., for reading a CD-ROM disk or to read from or write to other optical media. The storage device may be connected to the system bus by a storage device interface, such as a hard disk drive interface, a magnetic disk drive interface and an optical drive interface. Although this description of computer-readable media refers to a hard disk, a removable magnetic disk and a CD-ROM disk, it should be appreciated that other types of media that are readable by a computer system and that are suitable to the desired end purpose may be used, such as magnetic cassettes, flash memory cards, digital video disks, etc.

FIG. 5 shows an embodiment of a system for synthesizing a radiolabeled tracer. In this embodiment, two-way loading of the QMA cartridge is used.

The system may comprise a source of $^{18}$O—$H_2O$ with $^{18}$F (a), which may be obtained from the bombardment of target water, [O-18]$H_2O$, in a cyclotron. It may also comprise a source of acetonitrile (MeCN) (b), which may be used to prepare the water solution for elution. The sources of $^{18}$O—$H_2O$ with $^{18}$F and MeCN may be in communication with a first valve, which may be a check valve; for example, a 3-way check valve. The system may also comprise a second valve, which may also be a 3-way check valve. These valves are in communication with at least one ion exchange column, which may be a QMA column. As shown in FIGS. 5 and 6, the ion exchange column may be positioned between the first and second valves. The system may also comprise at least one waste container or disposal area. The system may also comprise at least one shield configured to shield a user from radioactivity.

The system also may include an apparatus for the transfer of materials such as reagents, products and/or intermediates. In one embodiment, the system is similar with that described in the previous part of the present disclosure. That system provides for the remote transfer of reagents, products, intermediates, etc. The system/apparatus is preferably located behind the radioactive shield and can be operated by an operator on the other side of the radioactive shield thus avoiding or limiting the user's exposure to radiation.

In the embodiment shown in FIG. 5, the apparatus comprises a plurality of containers: a first container accommodating processing such as heating, cooling, and stirring, a second container as an intermediate vial, and a third container for holding a plurality of reagents.

The third containers may include, for example, three containers (A, B, C), which are connected in series; in particular, and are all in communication with one another while container A is the only container in direct communication with the second valve of the 3-way check valves. These containers may contain any reagents, intermediates and/or products. Such reagents may include HCl, anion eluting solvent in MeCN/$H_2O$, alkyne with a good leaving group, $^{18}$F-fluoride, Kryptofix™ 2.2.2, $K_2CO_3$, etc. Two containers among the three containers may have a separate reagent and one is empty as a spare. In other embodiments, more or less containers may be used and more than one reagent may be in each container.

As shown in FIG. 5, also in communication with the plurality of containers is a pressure source such as a pneumatic device. The pressure source may provide pressurized gas or liquid to the system. In the embodiment shown in FIG. 5, the pressure source also provides gas to container A, which drives the contents out and toward the first container, which is described below.

The first container may comprise a tracer precursor such as mannose triflate with acetonitrile. The first container may be a number of structures including a vial and/or a reaction chamber. The first container may be in communication with or adjacent a heat or cooling source and may have a stirrer. The first container may hold about 0.1 to about 10 mL of radioactive evaporate. In some embodiments, the first container may comprise a click chemistry mixture. Such a click chemistry mixture may be the result of a reaction of the alkyne with a good leaving group, $^{18}F$-fluoride, Kryptofix™ 2.2.2, $K_2CO_3$ and MeCN of the primary container. In other embodiments, other click chemistry reaction products or intermediates may be contained in the secondary container.

As described above, the first container may comprise at least two lines (Line a and Line b), which are in communication with products, reactants, intermediates, etc. in the first container. Containers A-C are in communication with the first container via at least one first line. This first line may be connected to Line a. At least a portion of each of Line a or Line b may be within an interior of the container. These lines are moveable within the container; preferably toward or away from the bottom of the first container or within or out of the contents of the container. As shown in FIG. 5, in one position, one of the lines is positioned closer to the bottom of the first container than the other line. The "bottom" may change depending on the orientation of the container. As shown, the apparatus and the container are upright; or substantially perpendicular to a ground plane.

In the embodiment shown in FIG. 5, Line b is positioned closer to the bottom than Line a. The container may contain reagents, products, intermediates, etc. In other embodiments, either line may be outside of the container entirely. As explained in more detail below, the first line and the second line may be moved by different means. These include mechanical means, solenoids, hydraulics, electronic means that may be controlled by a controller in communication with a computer, etc. Preferably, these means do not require direct operator intervention so as to limit or eliminate user exposure to radiation. Because the unit as set forth in the present disclosure is controlled remotely behind leaded shielding, the operator is protected from radioactive exposure. In the embodiments shown in FIGS. 5 and 6, the means is a pneumatic device.

The first container may contain reagents, intermediates and/or products. In one embodiment, it contains a click mixture, as a result of a click chemistry process. In the embodiments shown in FIGS. 5 and 6, the first container comprises a vial preloaded with MeCN and mannose triflate.

Various apparatuses may be in communication with or connected to the first container. As shown in FIG. 5, these may be an anion exchange column, C18 and $Al_2O_3$ cartridges, which may be included to remove unreacted $^{18}F$ ion. At least one vent and a radioactive detector may also be connected to the first container.

In communication with the first container, via the cartridges, may be a collection container (second container) for collecting finished product. In the system shown in FIGS. 5 and 6, this is $^{18}F$-FDG. Of course, this will contain other products if other molecules are synthesized.

As provided above, a pressure source may provide gas pressure to the third container (series of containers A-C). The pressurized gas causes the reagents, products and/or intermediates to be moved through the first line and, if the valve is open, to the first container. When Line b is not in communication with the reagents, products, intermediates, etc. (raised above the level of the solution), none of the contents in the secondary vial are transferred out of the first container.

After the gas push is completed, the gas flow may be stopped or reduced. The contents of the first container may now be left to react at various temperatures and times. The contents may optionally be agitated via stirring, heated or cooled or pressurized. If the pneumatic device is connected to a radioactivity detector, the amount of radioactivity in the first container may be monitored.

FIG. 6 shows another embodiment of a system according to the present disclosure. The system is essentially the same as that shown in FIG. 5, except that containers A-C are not connected in series. In the FIG. 6 embodiment, containers B and C are connected and container A is separated from containers B and C. In addition, two-way loading of the QMA is not used.

The system in FIG. 6 may comprise a source of $^{18}O$—H2O with $^{18}F$ and MeCN. Similarly, the system may comprise a first 3-way check valve and a second 3-way check valve, an ion exchange column (e.g., QMA) and a waste container. Unlike the system of FIG. 5, the system of FIG. 6 comprises a third 3-way check valve. In addition, in the system of FIG. 6, the anion eluting solvent in MeCN/$H_2O$ (container A) is in communication with the second valve and containers B and C are in communication with the third valve. Containers B and C are in series with container B in direct communication with the third valve. As in the system of FIG. 5, in the system of FIG. 6, the first container may contain lines (a, b) moveable within the first container. The operation of these lines and the remotely operable transfer apparatus generally, is described in the previous part of the present disclosure. The first container may be in communication with a vent, anion exchange C18 and $Al_2O_3$ cartridges, a filter and a collection container.

The following illustrates one method that may be used with the systems of FIGS. 5 and/or 6.

With the first valve open, the target water is passed through the ion exchange cartridge (QMA) to trap the F-18 out of a dilute solution, after the cartridge has been prepped, which may include washing the cartridge with an organic solvent (e.g., anhydrous acetonitrile) and then drying the cartridge (e.g., by passing an inert gas through the cartridge.)

With the second valve open, gas pressure is applied to containers A-C. Container A provides anion eluting solvent of water and an organic solvent, for example, MeCN/$H_2O$, through the second valve and then through QMA. Water, for elution from the anion exchange cartridge however, may range from about 0.1% to about 5%. The amount of base (e.g., $K_2CO_3$) may be about 0.1 to about 50 mg/mL.

The anion eluting solvent elutes the $^{18}F$ from the anion exchange column. The eluting solvent may comprise salts, such as $K_2CO_3$, dissolved in water. An additive such as the potassium crown ether Kryptofix™ K222, which is dissolved in anhydrous acetonitrile, may be used in conjunction with aqueous $K_2CO_3$ to facilitate the elution of $^{18}F$-fluoride. At this point, the system may be employed to dry the mixture as in conventional systems.

However, the system is operable to carry out reactions without the conventional drying step. A probe precursor may then combine with the $^{18}$F solution so as to arrive at an $^{18}$F-labeling solution which has water in an amount of from about 0.1% to 2.0%. This can be accomplished, for example, by diluting either the probe precursor or the $^{18}$F solution, or both, with an appropriate amount of organic solvent. In the embodiments shown in FIGS. 5 and 6, the precursor (e.g., mannose triflate) is contained within the first container. As such, $^{18}$F is provided to the first container via the first line, where it is combined with the precursor. The reaction may then be heated at 90° C. for 45 seconds. The MeCN may then be removed under reduced pressure and heat.

HCl may then be introduced into the reaction mixture. Gas pressure may be provided to container B. With the second valve open, HCl is provided to the first container through QMA and first line. The HCl may be concentrated at 2M and about 1 mL may be added. The reaction may then be heated at 100° C. for 480 seconds. The crude reaction mixture may then be diluted with water and passed through a series of cartridges (Al$_2$O$_3$, C18, ICH—HCO$_3$) to afford 445 mCi (60% yield, decay corrected) 65 minutes after the end of bombardment EOB.

Because the amount of water is controlled by the elution of fluoride, the percentage of water remains the same from run to run, making the radiochemistry more consistent. Also, because the fluorination appears to tolerate the presence of a small range of water, there is no need to dry the fluoride. As a beneficial consequence of eliminating the drying step, the decomposition of temperature-sensitive reagents such as Kryptofix™ K222 and tetrabutyl ammonium bicarbonate ("TBAB") are minimized.

Next, the crude reaction mixture of the first container may be diluted with water and passed through a series of cartridges (Al$_2$O$_3$, C18, ICH—HCO$_3$) to afford 445 mCi (60% yield, decay corrected) 65 minutes after EOB. Radio-TLC indicated that purity of $^{18}$F-FDG was >95%.

It is noted that the system may be on a macrofluidic or microfluidic scale. A "microfluidic device" or "microfluidic chip" is a unit or device that permits the manipulation and transfer of small amounts of liquid (e.g., microliters or nanoliters) into a substrate comprising micro-channels and micro-compartments. The microfluidic device may be configured to allow the manipulation of liquids, including reagents and solvents, to be transferred or conveyed within the micro-channels and reaction chamber using mechanical or non-mechanical pumps. Microfluidic devices permit manipulation of extremely small volumes of liquid, for example on the order of about 1 mL to about 1 μL. In a microfluidic system, the containers (such as the vials) may contain a volume of about 5 μL to about 1,000 μL. In a macrofluidic device, the volumes are greater. In the present disclosure, the containers may hold at least one mL; more specifically, about 1 mL to about 50 mL, depending on the synthesis. In some embodiments, the containers may hold up to about 10 mL.

What is described is a platform for labeling that is simple in design, cost-efficient, flexible in adapting to different labeling protocols and has components that do not require cleaning. Cleaning may be avoided due to the two-way loading and unloading of the QMA and the ability to fluorinate in aqueous environments. It is also noted that several components may be disposable. These may include the primary containers, the secondary container, the anion exchange, C18, Al$_2$O$_3$ cartridges, sterile filter, FDG container, QMA, and the lines (a and b).

It will be understood that the components shown in FIGS. 5 and 6 may be within an apparatus of almost any size or shape. In addition, there may be multiple "sets" of the synthesis equipment shown in FIGS. 5 and 6. Providing multiple sets of equipment allows for multiple runs.

Figure 7:
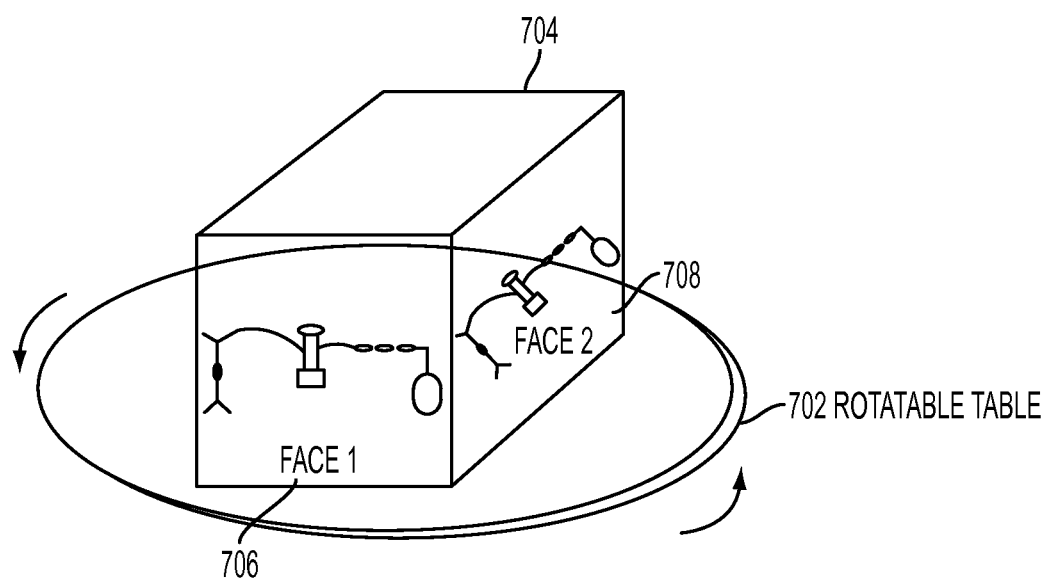
FIG. 7 shows another embodiment as set forth in the present disclosure.

As shown in FIG. 7, there may be four sets of synthesis equipment on a stand 704 such as a cube or rectangular box. (In FIG. 7, the sets are simplified to show their relative location on the overall apparatus.) Each set of equipment may be arranged on or adjacent to each face of the cube or box. The side faces, such as face 1 (706), face 2 (708), face 3 (not shown in FIG. 7), and face 4 (not shown in FIG. 7), may each have one set of equipment. The top and bottom faces may contain equipment or may simply be lids. As shown in FIG. 7, the apparatus may be moveable. This may be especially advantageous where there are multiple sets of synthesis equipment. As shown in FIG. 7, the apparatus may be on a rotatable table 702. Rotation of the table allows a user to easily access the different sets of equipment. It will be understood that other means may be used to move the apparatus, depending on the number and location of the equipment sets.

The platform as set forth in the present disclosure is simpler than those known in the art. For example, the commercially-available Coincidence FDG synthesis module has a number of required features that are not required in the system as set forth in the present disclosure. (The Coincidence system is representative of others known in the art.)

First, the Coincidence system requires the use of vacuum to transfer reagents throughout the system. The system as set forth in the present disclosure is capable of functioning without a vacuum; removing a potential liability from the system.

Secondly, the transfer line in and out of the reaction in the commercial system is a shared line. In other words, the reagents come in and the products leave via the same line. This can cause cross contamination within the system. The system as set forth in the present disclosure has separate "in" and "out" lines.

Third, there is a dramatic reduction in the overall number of valves in the system as set forth in the present disclosure versus those known in the art. For example, on just the reagent and delivery platform in the Coincidence system, there are 15 valves. The system, as set forth in the present disclosure, has less than 10 valves. Fewer valves mean fewer points of liability within the system.

In addition, the embodiments as set forth in the present disclosure all support aqueous fluorination chemistry, which is not readily or at all accomplished on existing systems. An example of this type of chemistry is described in PCT/US2011/31681.

Examples

Preparation of the K$_2$CO$_3$ and Kryptofix K222 Elution Solvent:

K$_2$CO$_3$ (11 mg) was dissolved in water (0.1 mL). Kryptofix™ K222 (100 mg) was dissolved in acetonitrile (1.9 mL). The solutions were mixed and 0.4 mL, or 2×0.2 mL, was used to elute $^{18}$F-fluoride from an anion exchange cartridge.

Loading and Drying of the Anion Exchange Cartridge:

An Activated Anion Exchange Cartridge (QMA Lite, Bicarbonate Form), was Loaded with $^{18}$F-fluoride in $^{18}$O-water. The cartridge was then washed with anhydrous acetonitrile (3×1 mL) to remove residual moisture from the cartridge. The cartridge was then further dried by passing an inert gas (such as He) through the cartridge for approximately 30 to 90 seconds.

Elution of $^{18}$F-Fluoride from the Anion Exchange Cartridge:

After a solution of $^{18}$F-fluoride (up to 50 mCi per run) in $^{18}$O-water was passed through the ion-exchange column, a solution of $K_2CO_3$/Kryptofix™ K222 (0.4 mL or 2×0.2 mL) was passed through the anion exchange cartridge into a dried reaction vessel. An additional portion of anhydrous acetonitrile (0.6 mL) was added to the reaction vessel. This final step constitutes the formation of $^{18}$F-fluoride in a hydrous organic solution that was suitable for radiolabeling.

Synthesis of $^{18}$F-FDG

Synthesis of $^{18}$F-FDG (Entry 4):

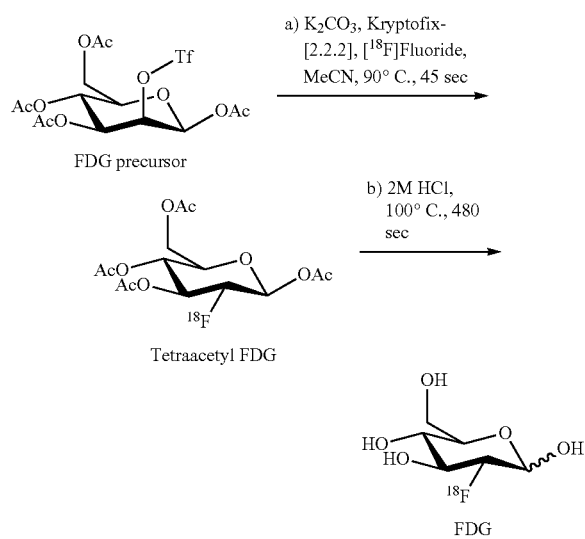

FDG precursor (mannose triflate, 50 mg) dissolved in acetonitrile (1.0 mL) is added to the reaction vessel containing the activated $^{18}$F-fluoride. The reaction is heated at 90° C. for 45 seconds. The MeCN is optionally removed under reduced pressure and heat. HCl (2M, 1 mL) is added and the reaction was heated at 100° C. for 480 seconds. The crude reaction mixture is diluted with water and passed through a series of cartridges ($Al_2O_3$, C18, ICH—HCO3) affording $^{18}$F-FDG.

Alternate Embodiments

Various alternate embodiments of the present invention will be discussed with reference to FIGS. 1-7.

One embodiment of the present invention is directed to a system for transferring chemical solutions. The system includes a primary container and a secondary container. A first line is in communication with both the primary container and the secondary container. The first line facilitates the flow of gas and/or liquid, or a combination of gas and liquid between the primary container and the secondary container. A valve, located upstream of the secondary container and downstream of the primary container, regulates flow within the first line. A second line is in communication with the secondary container. A pressure source is in communication with the primary container. The pressure source drives gas and/or liquid, or a combination of gas and liquid, to the secondary container via the first line. The first line and the second line can move within the secondary container.

Another embodiment of the present invention is directed to the system described above and also includes a source of chemical reagents in communication with the primary container.

Yet another embodiment of the present invention is directed to the system described above, wherein the primary container and the secondary container are configured to contain chemical reagents, reaction intermediates and/or reaction products and/or facilitate chemical reactions therein.

Yet another embodiment of the present invention is directed to the system described above, wherein the first line and the second line are configured to move within the secondary container either toward and/or away from the bottom of the secondary container.

Yet another embodiment of the present invention is directed to the system described above, wherein the pressure source provides pressurized gas to the source of chemical reagents, reaction intermediates and/or reaction products.

Yet another embodiment of the present invention is directed to the system described above, wherein the second line moves independently of the first line.

Yet another embodiment of the present invention is directed to the system described above and also includes a pneumatic device coupled to the first line and to the second line. The pneumatic device configured to move the first line and the second line.

Yet another embodiment of the present invention is directed to the system described above, wherein the pneumatic device is coupled to a controller. The pneumatic device is remotely operable using the controller.

Yet another embodiment of the present invention is directed to the system described above, wherein the secondary container is in communication with an HPLC load vial via the second line.

Yet another embodiment of the present invention is directed to the system described above, wherein the system is configured to synthesize radiolabeled tracers.

Yet another embodiment of the present invention is directed to the system described above, wherein the reagent sources include tetrabutyl ammonium bicarbonate, tetraethylammonium bicarbonate, $K_2CO_3$, K222, MeCN, Mannose Triflate, acids, bases or water.

Yet another embodiment of the present invention is directed to the system described above, wherein the first line and the second line are configured to move toward and away from a chemical solution when the chemical solution is in the secondary container.

Yet another embodiment of the present invention is directed to the system described above, wherein the first line is configured to move within the container between an "in" position, where the first line is in contact with the chemical solution, and an "out" position, where the first line is out of contact with the chemical solution. The second line is configured to move within the container between the "in" position and the "out" position.

Yet another embodiment of the present invention is directed to the system described above, and also includes a radioactive shield. The controller is outside of the shield and the primary and secondary containers are within the shield.

Yet another embodiment of the present invention is directed to the system described above, and used for synthesizing CP18 or K-5.

Yet another embodiment of the present invention is directed to an apparatus for transferring chemical solutions.

The apparatus includes a container configured to contain chemical reagents, reaction intermediates and/or reaction products. A first line is in communication with the container and the first line configured to deliver the chemical reagents, reaction intermediates and/or reaction products to the container. A second line is in communication with the container. The first line and second line are configured to move toward and away from the bottom of the container.

Yet another embodiment of the present invention is directed to the apparatus described above and also includes a pneumatic device coupled to the first line and to the second line. The pneumatic device configured to move the first line and the second line.

Yet another embodiment of the present invention is directed to the apparatus described above, wherein the pneumatic device is coupled to a controller such that the pneumatic device is remotely operable.

Yet another embodiment of the present invention is directed to the apparatus described above, wherein the first line and the second line move substantially vertically with respect to a ground plane.

Yet another embodiment of the present invention is directed to the apparatus described above, wherein the controller is in communication with a computer. The computer includes a non-transitory computer-readable medium.

Yet another embodiment of the present invention is directed to the apparatus described above and also includes at least one air valve in communication with the at least one pneumatic actuator.

Yet another embodiment of the present invention is directed to the apparatus described above and also includes a heater adjacent the container.

Yet another embodiment of the present invention is directed to the apparatus described above and also includes a cooling fan adjacent the container.

Yet another embodiment of the present invention is directed to the apparatus described above, wherein the container is positioned substantially vertically.

Yet another embodiment of the present invention is directed to the apparatus described above, wherein the container is substantially open at one end.

Yet another embodiment of the present invention is directed to the apparatus described above, and used for synthesizing CP18 or K-5.

Yet another embodiment of the present invention is directed to a method of transferring chemical solutions. The method includes providing a source of chemical reagents, reaction intermediates and/or products, providing a container and providing a pressure source configured to move chemical reagents, reaction intermediates and/or products into the container. The method also includes providing a first line in communication with the source of chemical reagents, reaction intermediates and/or products and the container and providing a second line in communication with the container. The first line and the second line are configured to move relative to the container. Additionally, the method includes positioning the first line so that it interacts with chemical reagents, reaction intermediates and/or products when the chemical reagents, reaction intermediates, and/or products are introduced into the container and positioning the second line so that it is excluded from interacting with the chemical reagents, reaction intermediates and/or products when the chemical reagents, reaction intermediates, and/or products are introduced into the container. Next, the method includes transferring the chemical reagents, reaction intermediates and/or products to the container through the first line, via pressure from the pressure source, such that the first line is in contact with the chemical reagents, reaction intermediates and/or products and the second line is out of contact with the chemical reagents, reaction intermediates and/or products and also moving the first line out of contact with the chemical reagents, reaction intermediates and/or products. The method also includes moving the second line in contact with the chemical reagents, reaction intermediates and/or products.

Yet another embodiment of the present invention is directed to the method described above and also includes closing the valve after the transferring step.

Yet another embodiment of the present invention is directed to the method described above and also includes providing pressurized gas from the pressure source after the transferring step.

Yet another embodiment of the present invention is directed to the method described above and also includes opening the valve after the transferring step.

Yet another embodiment of the present invention is directed to the method described above and also includes providing a primary container in communication with and downstream of the source of chemical reagents, reaction intermediates and/or products and upstream and in communication with the container, via the first line.

Yet another embodiment of the present invention is directed to the method described above, wherein the source of chemical reagents, reaction intermediates and/or products includes a source of chemical reagents. The chemical reagents include tetrabutyl ammonium bicarbonate, tetraethylammonium bicarbonate, $K_2CO_3$, K222, MeCN, Mannose Triflate, acids, bases or water.

Yet another embodiment of the present invention is directed to the method described above, wherein the steps of moving the first line and second line are performed by a pneumatic device configured to be remotely operable.

Yet another embodiment of the present invention is directed to the method described above, wherein the method is configured for synthesizing CP18 or K-5.

Yet another embodiment of the present invention is directed to a system for synthesizing a tracer. The tracer system includes a source of a solution, which includes a radionuclide, and a first container comprising a tracer precursor. The first container is in communication with the source of solution comprising radionuclide. The tracer system also includes a second container in communication with the first container. The second container is configured to store the tracer. A valve is located downstream of the source of solution comprising radionuclide and located upstream of the first container.

Yet another embodiment of the present invention is directed to the tracer system described above and also includes an apparatus configured to separate the radionuclide from the solution. The apparatus is disposed downstream of the source of solution comprising a radionuclide and upstream of the first container.

Yet another embodiment of the present invention is directed to the tracer system described above and also includes a third container in communication with the first container. The third container is disposed upstream of the apparatus configured to separate the radionuclide from the solution.

Yet another embodiment of the present invention is directed to the tracer system described above, wherein the third container comprises a plurality of containers connected in series.

Yet another embodiment of the present invention is directed to the tracer system described above, wherein the third container includes an eluting solvent to elute radionuclide from the apparatus configured to separate the radionuclide from the solution.

Yet another embodiment of the present invention is directed to the tracer system described above, wherein all three containers of the third container are upstream of the source of solution comprising a radionuclide.

Yet another embodiment of the present invention is directed to the tracer system described above, wherein one container is disposed upstream of the source of solution comprising a radionuclide and two containers are located downstream of the source of solution comprising a radionuclide.

Yet another embodiment of the present invention is directed to the tracer system described above and also includes a third valve downstream of the two containers and downstream of the first container.

Yet another embodiment of the present invention is directed to the tracer system described above, wherein one container comprises an anion eluting solvent in MeCN/H$_2$O.

Yet another embodiment of the present invention is directed to the tracer system described above, wherein one container comprises aqueous HCl.

Yet another embodiment of the present invention is directed to the tracer system described above and also includes an anion exchange cartridge in communication with and downstream of the third container.

Yet another embodiment of the present invention is directed to the tracer system described above and also includes a filter system in communication with and downstream of the first container.

Yet another embodiment of the present invention is directed to the tracer system described above, wherein the first container is configured to comprise MeCN.

Yet another embodiment of the present invention is directed to the tracer system described above and also includes a gas source in communication with the third container. The gas source is configured to push contents in the three containers toward the first container.

Yet another embodiment of the present invention is directed to the tracer system described above and also includes an apparatus for transferring chemical solutions, the apparatus includes a first line in communication with the first container, the first line configured to deliver chemical reagents, reaction intermediates and/or reaction products to the first container. A second line is in communication with the first container. The first line and second line are configured to move toward and away from the bottom of the first container.

Yet another embodiment of the present invention is directed to the tracer system described above, wherein a drying apparatus is excluded from the system.

Yet another embodiment of the present invention is directed to the tracer system described above, wherein at least one component is disposable.

Yet another embodiment of the present invention is directed to the tracer system described above and also includes a drying apparatus in communication with an ion exchange column.

Yet another embodiment of the present invention is directed to a system for synthesizing a tracer. The system includes a source of a solution comprising a radionuclide. The system also includes a first container having a tracer precursor. The first container is in communication with the source of solution comprising radionuclide. The system also includes an apparatus configured to separate the radionuclide from the solution. The apparatus being disposed downstream of the source of solution comprising radionuclide and upstream of the first container. The system also includes a source of eluting solvent configured to elute radionuclide separated by the apparatus configured to separate the radionuclide from the solution.

Yet another embodiment of the present invention is directed to the system for synthesizing a tracer in which the eluting solvent source is disposed upstream of the apparatus configured to separate the radionuclide from the solution.

Yet another embodiment of the present invention is directed to the system for synthesizing a tracer and also includes a second valve positioned between the eluting solvent source and the apparatus configured to separate the radionuclide from the solution.

Yet another embodiment of the present invention is directed to the system for synthesizing a tracer that also includes a first valve disposed downstream of the source of a solution comprising a radionuclide and downstream of the apparatus configured to separate the radionuclide from the solution and upstream of the first container.

Yet another embodiment of the present invention is directed to the system for synthesizing a tracer and also includes a third container in communication with the first container. The third container is disposed upstream of the apparatus configured to separate the radionuclide from the solution.

Yet another embodiment of the present invention is directed to the system for synthesizing a tracer, wherein the third container includes the source of eluting solvent.

Yet another embodiment of the present invention is directed to the system for synthesizing a tracer, wherein the source of eluting solvent further comprises aqueous HCl.

Yet another embodiment of the present invention is directed to the system for synthesizing a tracer and also includes a heat source in communication with the first container.

Yet another embodiment of the present invention is directed to the system for synthesizing a tracer, wherein the first container comprises a tracer precursor.

Yet another embodiment of the present invention is directed to the system for synthesizing a tracer and also includes a lead shield.

Yet another embodiment of the present invention is directed to the system for synthesizing a tracer and also includes an apparatus for transferring chemical solution. The apparatus includes a first line in communication with the first container, the first line configured to deliver chemical reagents, reaction intermediates and/or reaction products to the first container. The apparatus also includes a second line in communication with the first container. The first line and second line are configured to move toward and away from the bottom of the first container.

Yet another embodiment of the present invention is directed to the system for synthesizing a tracer and also includes a gas source in communication with the third container.

Yet another embodiment of the present invention is directed to the system for synthesizing a tracer and also includes an anion exchange apparatus downstream of the first container and upstream of the second container.

Yet another embodiment of the present invention is directed to the system for synthesizing a tracer and includes a second container in communication with the first container, the second container configured to store the tracer.

Yet another embodiment of the present invention is directed to a method for synthesizing an $^{18}$F-labeled probe. This includes a step of eluting an amount of $^{18}$F with a first solvent which includes a predetermined amount of water and at least one organic solvent, wherein the $^{18}$F elutes as an $^{18}$F solution. The method also includes a step of using the $^{18}$F solution to perform $^{18}$F-labeling in the presence of at least one labeling reagent and at least one phase transfer catalyst so as to generate the $^{18}$F-labeled probe. Drying the $^{18}$F is excluded starting from a time when the eluting step is performed and ending at a time when the $^{18}$F-labeling step is performed.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

Throughout the specification and claims, the following terms take at least the meanings explicitly associated herein, unless the context dictates otherwise. The meanings identified below do not necessarily limit the terms, but merely provide illustrative examples for the terms. In the text, the terms "comprising", "comprise", "comprises" and other forms of "comprise" can have the meaning ascribed to these terms in U.S. Patent Law and can mean "including", "include", "includes" and other forms of "include." The term "contains" or other forms thereof, as used herein, is synonymous with "comprises" or "includes"; it is similarly inclusive or open-ended and does not exclude additional, unrecited elements or steps. The term "composed" or other forms thereof, as used herein, denotes that some embodiments or implementations may exclude unspecified materials, compounds, elements, components, or the like (e.g., other than, for example, impurities, trace compounds, or the like), and that some embodiments may not exclude other unspecified materials, compounds, elements, components, or the like; for example, other unspecified materials, compounds, elements, may be included provided they do not adversely affect the desired characteristics of the specified material, compound, element, component, or the like, or otherwise do not materially alter the basic and novel characteristics of the embodiment or implementation. The phrase "an embodiment" as used herein does not necessarily refer to the same embodiment, though it may. In addition, the meaning of "a," "an," and "the" include plural references; thus, for example, "an embodiment" is not limited to a single embodiment but refers to one or more embodiments. As used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise.

It will be appreciated by those skilled in the art that the foregoing brief description and the following detailed description are exemplary (i.e., illustrative) and explanatory of the subject matter as set forth in the present disclosure, but are not intended to be restrictive thereof or limiting of the advantages which can be achieved by the present disclosure in various implementations. Additionally, it is understood that the foregoing summary and ensuing detailed description are representative of some embodiments as set forth in the present disclosure, and are neither representative nor inclusive of all subject matter and embodiments within the scope as set forth in the present disclosure. Thus, the accompanying drawings, referred to herein and constituting a part hereof, illustrate embodiments of this disclosure, and, together with the detailed description, serve to explain principles of embodiments as set forth in the present disclosure.

We claim:

1. A system for transferring chemical solutions, the system comprising:
    a primary container;
    a secondary container; where the primary container and the secondary container are reaction pots in which a reaction is conducted;
    a third container in communication with the primary container, wherein the third container is disposed upstream of the primary container and configured to separate a radionuclide from the solution;
    a first line in communication with the primary container and the secondary container, the first line configured to facilitate the flow of gas and/or liquid between the primary container and the secondary container;
    a valve upstream of the secondary container and downstream of the primary container, the valve configured to regulate flow within the first line;
    a second line in communication with the secondary container; and
    a pressure source in communication with the primary container, the pressure source configured to drive gas and/or liquid to the secondary container via the first line; wherein the first line and the second line are configured to move within the secondary container; and wherein the first line and the second line are configured to move independently toward and away from a chemical solution when the chemical solution is in the secondary container; and
    a radioactivity detector that is configured to measure radioactivity in the first container.

2. The system of claim 1, wherein the secondary container is in communication with an HPLC load vial via the second line.

3. The system of claim 1, wherein the system is configured to synthesize radiolabeled tracers.

4. A method of transferring chemical solutions, the method comprising:
    providing a source of chemical reagents, reaction intermediates and/or products; where the chemical reagents, reaction intermediates and/or products are radioactive;
    providing a container; where the container is a reaction pot in which a reaction is conducted; where the container is sealed;
    providing a pressure source configured to move chemical reagents, reaction intermediates and/or products into the container;
    providing a first line in communication with the source of chemical reagents, reaction intermediates and/or products and the container;
    providing a second line in communication with the container, wherein the first line and the second line are configured to move relative to the container,
    positioning the first line so that it interacts with chemical reagents, reaction intermediates and/or products when the chemical reagents, reaction intermediates, and/or products are introduced into the container;
    positioning the second line so that it is excluded from interacting with the chemical reagents, reaction intermediates and/or products when the chemical reagents, reaction intermediates, and/or products are introduced into the container;
    transferring the chemical reagents, reaction intermediates and/or products to the container through the first line, via pressure from the pressure source, such that the first line is in contact with the chemical reagents, reaction intermediates and/or products and the second line is out of contact with the chemical reagents, reaction intermediates and/or products;

moving the first line out of contact with the chemical reagents, reaction intermediates and/or products; and moving the second line independent of the first line in contact with the chemical reagents, reaction intermediates or products; and where the first line and second line each contain needles that puncture the sealed container; and detecting radioactivity via a radioactivity detector.

5. The method of claim 4, further comprising closing the valve after the transferring step.

6. A system for synthesizing a tracer, the system comprising:
a source of a solution comprising a radionuclide;
a first container comprising a tracer precursor, the first container in communication with the source of solution comprising radionuclide;
a second container in communication with the first container, the second container configured to store the tracer; where the second container is sealed;
a first line in communication with the first container and the second container, the first line being configured to facilitate the flow of gas and/or liquid between the first container and the second container;
a second line in communication with the second container; wherein the first line and the second line are configured to move independently toward and away from a chemical solution when the chemical solution is in the secondary container; where the first line and second line each contain needles that puncture the sealed container;
a valve downstream of the source of solution comprising radionuclide and upstream of the first container; and
a radioactivity detector configured to measure radioactivity in the container.

7. The system of claim 6, further comprising an apparatus configured to separate the radionuclide from the solution, wherein the apparatus is disposed downstream of the source of solution comprising a radionuclide and upstream of the first container.

8. The system of claim 7, further comprising a third container in communication with the first container, wherein the third container is disposed upstream of the apparatus configured to separate the radionuclide from the solution.

9. The system of claim 8, wherein the third container is configured to comprise an eluting solvent configured to elute radionuclide from the apparatus configured to separate the radionuclide from the solution.

10. The system of claim 6, further comprising a gas source in communication with the third container, wherein the gas source is configured to push contents in the three containers toward the first container.

11. The system of claim 6, further comprising an apparatus for transferring chemical solutions, the apparatus comprising: a first line in communication with the first container, the first line configured to deliver chemical reagents, reaction intermediates and/or reaction products to the first container; and a second line in communication with the first container, wherein the first line and second line are configured to move toward and away from the bottom of the first container.

12. The system of claim 6, wherein at least one component is disposable.

13. A system for synthesizing a tracer, the system comprising:
a source of a solution comprising a radionuclide;
a first container comprising a tracer precursor, the first container in communication with the source of solution comprising radionuclide; where the first container is sealed;
an apparatus configured to separate the radionuclide from the solution, the apparatus being disposed downstream of the source of solution comprising radionuclide and upstream of the first container;
an apparatus for transferring chemical solution, the apparatus comprising: a first line in communication with the first container, the first line configured to deliver chemical reagents, reaction intermediates and/or reaction products to the first container; and a second line in communication with the first container, wherein the first line and second line are configured to independently move toward and away from the bottom of the first container; where the first line and second line each contain needles that puncture the sealed container;
a source of eluting solvent configured to elute radionuclide separated by the apparatus configured to separate the radionuclide from the solution; and
a radioactivity detector configured to measure radioactivity in the first container.

14. The system of claim 13, wherein the first container comprises a tracer precursor.

* * * * *